US012048706B2

(12) United States Patent
Reddy et al.

(10) Patent No.: US 12,048,706 B2
(45) Date of Patent: Jul. 30, 2024

(54) METHODS OF TREATING EPILEPSY OR STATUS EPILEPTICUS

(71) Applicant: Sage Therapeutics, Inc., Cambridge, MA (US)

(72) Inventors: Kiran Reddy, Boston, MA (US); Stephen J. Kanes, Swarthmore, PA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/592,244

(22) Filed: Feb. 3, 2022

(65) Prior Publication Data

US 2022/0152050 A1   May 19, 2022

Related U.S. Application Data

(63) Continuation of application No. 16/419,761, filed on May 22, 2019, now abandoned, which is a continuation of application No. 15/940,505, filed on Mar. 29, 2018, now abandoned, which is a continuation of application No. 13/972,851, filed on Aug. 21, 2013, now abandoned.

(60) Provisional application No. 61/789,491, filed on Mar. 15, 2013, provisional application No. 61/691,545, filed on Aug. 21, 2012.

(51) Int. Cl.
| A61K 31/10 | (2006.01) |
| A61K 9/00 | (2006.01) |
| A61K 9/107 | (2006.01) |
| A61K 31/57 | (2006.01) |
| A61K 31/573 | (2006.01) |
| A61K 45/06 | (2006.01) |
| A61M 5/20 | (2006.01) |

(52) U.S. Cl.
CPC ............ *A61K 31/573* (2013.01); *A61K 31/57* (2013.01); *A61K 45/06* (2013.01)

(58) Field of Classification Search
CPC ...... A61K 31/57; A61K 31/573; A61K 45/06; A61K 47/6951; A61K 9/0019; A61K 9/08; A61K 9/107; A61K 9/1075; A61K 9/127; A61K 9/1605; A61P 23/00; A61P 25/08; A61P 25/10; A61P 25/12; A61P 43/00

See application file for complete search history.

(56) References Cited

U.S. PATENT DOCUMENTS

| 3,117,142 A | 1/1964 | Candido et al. |
| 3,169,134 A | 2/1965 | Klimstra et al. |
| 3,580,937 A | 5/1971 | Campbell et al. |
| 3,865,939 A | 2/1975 | Jandacek |
| 3,943,124 A | 3/1976 | Phillipps et al. |
| 3,983,111 A | 9/1976 | Phillipps et al. |
| 4,071,625 A | 1/1978 | Grunwell et al. |
| 4,192,871 A | 3/1980 | Phillipps et al. |
| 5,719,197 A | 2/1998 | Kanios et al. |
| 5,925,630 A | 7/1999 | Upasani et al. |
| 5,939,545 A | 8/1999 | Upasani et al. |
| 6,143,736 A | 11/2000 | Upasani et al. |
| 6,245,757 B1 | 6/2001 | Chopp et al. |
| 6,277,838 B1 | 8/2001 | Upasani et al. |
| 6,376,531 B1 | 4/2002 | Bell |
| 6,455,516 B1 | 9/2002 | Backstrom et al. |
| 6,603,008 B1 | 8/2003 | Ando et al. |
| 6,780,853 B1 | 8/2004 | Upasani et al. |
| 7,060,255 B2 | 6/2006 | Rabinowitz et al. |
| 7,064,116 B2 | 6/2006 | Calogeropoulou et al. |
| 7,090,830 B2 | 8/2006 | Hale et al. |
| 7,138,387 B2 | 11/2006 | Pai et al. |
| 7,630,757 B2 | 12/2009 | Dorfmeister et al. |
| 7,816,074 B2 | 10/2010 | Smith et al. |
| 7,858,609 B2 | 12/2010 | Shaw et al. |
| 7,998,971 B2 | 8/2011 | Barlow et al. |
| 8,012,958 B2 | 9/2011 | Sabnani et al. |
| 8,618,087 B2 | 12/2013 | Shaw et al. |
| 8,697,678 B2 | 4/2014 | Goodchild et al. |
| 8,969,329 B2 | 3/2015 | Brinton et al. |
| 9,056,116 B2 | 6/2015 | Shaw et al. |
| 9,084,797 B2 | 7/2015 | Caufriez et al. |
| 9,339,508 B2 | 5/2016 | Baulieu et al. |

(Continued)

FOREIGN PATENT DOCUMENTS

| CA | 2443266 A1 | 8/2002 |
| CA | 2443466 A1 | 12/2002 |

(Continued)

OTHER PUBLICATIONS

Zolkowska et al., "Anticonvulsant Activity of Intravenous and Intramuscular Allopregnenalone". 1-25. 26a-30a. 26b-30b. American Epilepsy Society: 2012 Annual Meeting Abstracts.

Zolkowska et al., "Anticonvulsant activity of intravenous and intramuscular allopregnenalone," American Epilepsy Society, (Poster), UC Davis, University of California, (2012), 1 page.

Zonana et al., "The Neurobiology of Postpartum Depression", CNS Spectrums, (2005), pp. 792-799, 805.

Zsuzsa, "Neurological and psychiatric aspects of some endocrine diseases. The role of neurosteroids and neuroactive steroids", Medical Journal (2007), 148(41): pp. 1929-1937, machine translated into English.

(Continued)

*Primary Examiner* — Jean P Cornet

(74) *Attorney, Agent, or Firm* — Honigman LLP; Harold H. Fox; Jonathan P. O'Brien

(57) ABSTRACT

Described herein are methods of treating epilepsy or status epilepticus, e.g., convulsive status epilepticus, e.g., early status epilepticus, established status epilepticus, refractory status epilepticus, super-refractory status epilepticus, e.g., super-refractory generalized status epilepticus; non-convulsive status epilepticus, e.g., generalized status epilepticus, complex partial status epilepticus; generalized periodic epileptiform discharges; periodic lateralized epileptiform discharges; a seizure, e.g., acute repetitive seizures, cluster seizures, the method comprising administering to the subject a neuroactive steroid.

4 Claims, 2 Drawing Sheets

(56) References Cited

U.S. PATENT DOCUMENTS

| | | |
|---|---|---|
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,676,812 B2 | 6/2017 | Covey et al. |
| 9,725,481 B2 | 8/2017 | Martinez Botella et al. |
| 9,765,110 B2 | 9/2017 | Covey |
| 10,023,606 B2 | 7/2018 | Martinez Botella et al. |
| 10,172,871 B2 | 1/2019 | Martinez Botella et al. |
| 10,246,482 B2 | 4/2019 | Harrison et al. |
| 10,251,894 B2 | 4/2019 | Rogawski et al. |
| 10,322,139 B2 | 6/2019 | Reddy |
| 10,323,059 B2 | 6/2019 | Martinez Botella et al. |
| 10,329,320 B2 | 6/2019 | Robichaud et al. |
| 10,342,809 B2 | 7/2019 | Covey et al. |
| 10,342,810 B2 | 7/2019 | Martinez Botella et al. |
| 10,377,790 B2 | 8/2019 | Martinez Botella et al. |
| 10,391,106 B2 | 8/2019 | Martinez Botella et al. |
| 10,426,786 B2 | 10/2019 | Rogawski et al. |
| 10,426,837 B2 | 10/2019 | Robichaud et al. |
| 10,435,431 B2 | 10/2019 | Upasani et al. |
| 10,577,390 B2 | 3/2020 | Martinez Botella et al. |
| 10,745,436 B2 | 8/2020 | Harrison et al. |
| 10,774,108 B2 | 9/2020 | Martinez Botella et al. |
| 10,822,370 B2 | 11/2020 | Martinez Botella et al. |
| 10,870,677 B2 | 12/2020 | Martinez Botella et al. |
| 10,940,156 B2 | 3/2021 | Kanes et al. |
| 11,046,728 B2 | 6/2021 | Martinez Botella et al. |
| 11,124,538 B2 | 9/2021 | Robichaud et al. |
| 11,147,877 B2 | 10/2021 | Robichaud et al. |
| 11,149,057 B2 | 10/2021 | Harrison et al. |
| 11,236,121 B2 | 2/2022 | Watson et al. |
| 11,241,446 B2 | 2/2022 | Martinez Botella et al. |
| 11,261,211 B2 | 3/2022 | Martinez Botella et al. |
| 11,344,563 B2 | 5/2022 | Martinez Botella et al. |
| 11,396,525 B2 | 7/2022 | Robichaud et al. |
| 11,426,417 B2 | 8/2022 | Reddy |
| 11,498,940 B2 | 11/2022 | Martinez Botella et al. |
| 11,510,929 B2 | 11/2022 | Rogawski et al. |
| 11,530,237 B2 | 12/2022 | Martinez Botella et al. |
| 11,542,297 B2 | 1/2023 | Martinez Botella et al. |
| 11,554,125 B2 | 1/2023 | Kanes et al. |
| 11,634,453 B2 | 4/2023 | Blanco-Pillado et al. |
| 2002/0072509 A1 | 6/2002 | Stein et al. |
| 2002/0183293 A1 | 12/2002 | Banerjee et al. |
| 2002/0198174 A1 | 12/2002 | Lyons |
| 2003/0032638 A1 | 2/2003 | Kim et al. |
| 2005/0201888 A1 | 9/2005 | Amar et al. |
| 2006/0063707 A1 | 3/2006 | Baudry et al. |
| 2006/0198896 A1 | 9/2006 | Liversidge et al. |
| 2007/0014719 A1 | 1/2007 | Reading et al. |
| 2007/0020299 A1 | 1/2007 | Pipkin et al. |
| 2007/0081948 A1 | 4/2007 | Morton et al. |
| 2007/0287931 A1 | 12/2007 | Dilorenzo |
| 2008/0195160 A1 | 8/2008 | Wingeier et al. |
| 2008/0269183 A1 | 10/2008 | Mellon et al. |
| 2009/0074677 A1 | 3/2009 | Marx et al. |
| 2009/0130216 A1 | 5/2009 | Cartt et al. |
| 2009/0162441 A1 | 6/2009 | Bartus et al. |
| 2009/0198145 A1 | 8/2009 | Chow |
| 2009/0203658 A1 | 8/2009 | Marx et al. |
| 2009/0221544 A1 | 9/2009 | Stein et al. |
| 2009/0239942 A1 | 9/2009 | Cloyd |
| 2009/0325920 A1 | 12/2009 | Hoffman et al. |
| 2010/0136105 A1 | 6/2010 | Chen et al. |
| 2010/0234335 A1 | 9/2010 | Gravanis et al. |
| 2010/0297181 A1 | 11/2010 | Hanada et al. |
| 2010/0316678 A1 | 12/2010 | Goodchild |
| 2010/0317638 A1 | 12/2010 | Covey et al. |
| 2010/0331762 A1 | 12/2010 | Wingeier et al. |
| 2011/0054038 A1 | 3/2011 | Glozman |
| 2011/0152840 A1 | 6/2011 | Lee et al. |
| 2011/0288059 A1 | 11/2011 | Marx et al. |
| 2011/0306579 A1 | 12/2011 | Stein |
| 2011/0319386 A1 | 12/2011 | Barlow et al. |
| 2012/0142645 A1 | 6/2012 | Marx |
| 2012/0302535 A1 | 11/2012 | Caufriez et al. |
| 2012/0316146 A1 | 12/2012 | Goodchild et al. |
| 2013/0210783 A1 | 8/2013 | Marx et al. |
| 2013/0309306 A1 | 11/2013 | Rogawski et al. |
| 2014/0050789 A1 | 2/2014 | Rogawski et al. |
| 2014/0057885 A1 | 2/2014 | Reddy et al. |
| 2014/0058079 A1 | 2/2014 | Mensah-Nyagan et al. |
| 2014/0148412 A1 | 5/2014 | Hogenkamp |
| 2014/0235600 A1 | 8/2014 | Covey et al. |
| 2014/0322198 A1 | 10/2014 | Buchwald-Werner et al. |
| 2014/0343027 A1 | 11/2014 | Rogawski |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0290181 A1 | 10/2015 | Lee et al. |
| 2015/0291654 A1 | 10/2015 | Upasani et al. |
| 2015/0313915 A1 | 11/2015 | Rogawski et al. |
| 2015/0315230 A1 | 11/2015 | Covey et al. |
| 2016/0068563 A1 | 3/2016 | Martinez Botella et al. |
| 2016/0083417 A1 | 3/2016 | Martinez Botella et al. |
| 2016/0083418 A1 | 3/2016 | Martinez Botella et al. |
| 2016/0229887 A1 | 3/2016 | Martinez Botella et al. |
| 2016/0108080 A1 | 4/2016 | Martinez Botella et al. |
| 2016/0152658 A1 | 6/2016 | Martinez Botella et al. |
| 2017/0190732 A1 | 7/2017 | Covey et al. |
| 2017/0232006 A1 | 8/2017 | Covey et al. |
| 2017/0233432 A1 | 8/2017 | Martinez Botella et al. |
| 2017/0233433 A1 | 8/2017 | Martinez Botella et al. |
| 2017/0240589 A1 | 8/2017 | Martinez Botella et al. |
| 2017/0246191 A1 | 8/2017 | Martinez Botella et al. |
| 2017/0247406 A1 | 8/2017 | Harrison et al. |
| 2017/0319695 A1 | 11/2017 | Robichaud et al. |
| 2017/0342102 A1 | 11/2017 | Martinez Botella et al. |
| 2017/0342103 A1 | 11/2017 | Upasani et al. |
| 2017/0348326 A1 | 12/2017 | Reddy |
| 2017/0348327 A1 | 12/2017 | Kanes et al. |
| 2018/0037602 A1 | 2/2018 | Robichaud et al. |
| 2018/0050005 A1 | 2/2018 | DiMauro et al. |
| 2018/0050107 A1 | 2/2018 | DiMauro et al. |
| 2018/0051052 A1 | 2/2018 | Martinez Botella et al. |
| 2018/0064728 A1 | 3/2018 | Chang et al. |
| 2018/0071315 A1 | 3/2018 | Cashman et al. |
| 2018/0133229 A1 | 5/2018 | Rogawski et al. |
| 2018/0141971 A1 | 5/2018 | Martinez Botella et al. |
| 2018/0153906 A1 | 6/2018 | Rogawski et al. |
| 2018/0179247 A1 | 6/2018 | Botella et al. |
| 2018/0193357 A1 | 7/2018 | Rogawski et al. |
| 2018/0215779 A1 | 8/2018 | Martinez Botella et al. |
| 2018/0235916 A1 | 8/2018 | Kaufman et al. |
| 2018/0256726 A1 | 9/2018 | Rogawski |
| 2018/0296487 A1 | 10/2018 | Saporito et al. |
| 2018/0311258 A1 | 11/2018 | Robichaud et al. |
| 2018/0311262 A1 | 11/2018 | Martinez Botella et al. |
| 2018/0369171 A1 | 12/2018 | Pinna et al. |
| 2019/0008873 A1 | 1/2019 | Salituro et al. |
| 2019/0038639 A1 | 2/2019 | Reddy et al. |
| 2019/0112331 A1 | 4/2019 | Botella et al. |
| 2019/0142845 A1 | 5/2019 | Rogawski et al. |
| 2019/0160078 A1 | 5/2019 | Masuoka et al. |
| 2019/0169226 A1 | 6/2019 | Harrison et al. |
| 2019/0177358 A1 | 6/2019 | Martinez Botella et al. |
| 2019/0177359 A1 | 6/2019 | Watson et al. |
| 2019/0233465 A1 | 8/2019 | Robichaud et al. |
| 2019/0247402 A1 | 8/2019 | Reddy |
| 2019/0248831 A1 | 8/2019 | Robichaud et al. |
| 2019/0269699 A1 | 9/2019 | Reddy |
| 2019/0337975 A1 | 11/2019 | Bryson et al. |
| 2019/0350944 A1 | 11/2019 | Salituro et al. |
| 2020/0016178 A1 | 1/2020 | Martinez Botella et al. |
| 2020/0017542 A1 | 1/2020 | Martinez Botella et al. |
| 2020/0024301 A1 | 1/2020 | Martinez Botella et al. |
| 2020/0024302 A1 | 1/2020 | Martinez Botella et al. |
| 2020/0048300 A1 | 2/2020 | Martinez Botella et al. |
| 2020/0113916 A1 | 4/2020 | Covey et al. |
| 2020/0113917 A1 | 4/2020 | Kanes et al. |
| 2020/0147071 A1 | 5/2020 | Jindal |
| 2020/0155522 A1 | 5/2020 | Osten et al. |
| 2020/0155576 A1 | 5/2020 | Martinez Botella et al. |

(56) References Cited

U.S. PATENT DOCUMENTS

| | | |
|---|---|---|
| 2020/0171049 A1 | 6/2020 | Kanes et al. |
| 2020/0179350 A1 | 6/2020 | During |
| 2020/0179351 A1 | 6/2020 | During |
| 2020/0179403 A1 | 6/2020 | Aimetti et al. |
| 2020/0188412 A1 | 6/2020 | Bryson et al. |
| 2020/0215078 A1 | 7/2020 | Rogawski et al. |
| 2020/0223884 A1 | 7/2020 | Upasani et al. |
| 2020/0246459 A1 | 8/2020 | Robichaud et al. |
| 2020/0253985 A1 | 8/2020 | Kanes et al. |
| 2020/0276209 A1 | 9/2020 | Colquhoun et al. |
| 2020/0281943 A1 | 9/2020 | Hoffmann et al. |
| 2020/0306262 A1 | 10/2020 | Doherty |
| 2020/0306265 A1 | 10/2020 | Kanes et al. |
| 2020/0354399 A1 | 11/2020 | Robichaud et al. |
| 2020/0377547 A1 | 12/2020 | Salituro et al. |
| 2020/0392177 A1 | 12/2020 | Martinez Botella et al. |
| 2021/0017218 A1 | 1/2021 | Martinez Botella et al. |
| 2021/0040141 A1 | 2/2021 | Upasani et al. |
| 2021/0061848 A1 | 3/2021 | Martinez Botella et al. |
| 2021/0061850 A1 | 3/2021 | Martinez Botella et al. |
| 2021/0087223 A1 | 3/2021 | Martinez Botella et al. |
| 2021/0094981 A1 | 4/2021 | Harrison et al. |
| 2021/0100817 A1 | 4/2021 | Rogawski et al. |
| 2021/0101928 A1 | 4/2021 | Robichaud et al. |
| 2021/0113590 A1 | 4/2021 | Robichaud et al. |
| 2021/0139531 A1 | 5/2021 | Botella et al. |
| 2021/0308149 A1 | 10/2021 | Covey et al. |
| 2021/0338692 A1 | 11/2021 | Kanes et al. |
| 2021/0340172 A1 | 11/2021 | Blanco-Pillado et al. |
| 2021/0347812 A1 | 11/2021 | Robichaud et al. |
| 2021/0363175 A1 | 11/2021 | Salituro et al. |
| 2021/0369734 A1 | 12/2021 | Doherty |
| 2021/0403502 A1 | 12/2021 | Harrison et al. |
| 2022/0023313 A1 | 1/2022 | Kanes et al. |
| 2022/0098231 A1 | 3/2022 | Salituro et al. |
| 2022/0110949 A1 | 4/2022 | Doherty et al. |
| 2022/0110950 A1 | 4/2022 | Martinez Botella et al. |
| 2022/0152050 A1 | 5/2022 | Reddy et al. |
| 2022/0169674 A1 | 6/2022 | Watson et al. |
| 2022/0213137 A1 | 7/2022 | Martinez Botella et al. |
| 2022/0220150 A1 | 7/2022 | Martinez Botella et al. |
| 2022/0315621 A1 | 10/2022 | Robichaud et al. |
| 2022/0323462 A1 | 10/2022 | Kanes et al. |
| 2022/0372067 A1 | 11/2022 | Blanco-Pillado et al. |
| 2022/0380405 A1 | 12/2022 | Salituro et al. |
| 2023/0018765 A1 | 1/2023 | Kanes et al. |
| 2023/0021308 A9 | 1/2023 | Robichaud et al. |
| 2023/0046825 A1 | 2/2023 | Blanco-Pillado et al. |
| 2023/0057130 A1 | 2/2023 | Watson et al. |
| 2023/0085354 A1 | 3/2023 | Robichaud et al. |
| 2023/0113666 A1 | 4/2023 | Martinez Botella et al. |
| 2023/0116347 A1 | 4/2023 | Robichaud et al. |

FOREIGN PATENT DOCUMENTS

| | | |
|---|---|---|
| CN | 1190404 A | 8/1998 |
| CN | 104136452 A | 11/2014 |
| EP | 0233849 A1 | 8/1987 |
| EP | 0656365 A1 | 6/1995 |
| EP | 0808325 A1 | 11/1997 |
| EP | 1038880 A2 | 9/2000 |
| GB | 1430942 A | 4/1976 |
| GB | 1570394 A | 7/1980 |
| GB | 1581234 A | 12/1980 |
| WO | 1991011172 A1 | 8/1991 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 9526325 A2 | 10/1995 |
| WO | 1996003421 A1 | 2/1996 |
| WO | 1996016076 A1 | 5/1996 |
| WO | 9640043 A2 | 12/1996 |
| WO | 1997003677 A1 | 2/1997 |
| WO | 9805337 A1 | 2/1998 |
| WO | 1999045931 A1 | 9/1999 |
| WO | 2002030409 A2 | 4/2002 |
| WO | 2004019953 A1 | 3/2004 |
| WO | 2005105822 A2 | 11/2005 |
| WO | 2006102644 A2 | 9/2006 |
| WO | 2007062266 A2 | 5/2007 |
| WO | 2008128049 A2 | 10/2008 |
| WO | 2008157460 A1 | 12/2008 |
| WO | 2009088530 A1 | 7/2009 |
| WO | 2010003391 A2 | 1/2010 |
| WO | 2010042925 A2 | 4/2010 |
| WO | 2010063030 A2 | 6/2010 |
| WO | 2010107815 A1 | 9/2010 |
| WO | 2011088503 A1 | 7/2011 |
| WO | 2012059456 A1 | 5/2012 |
| WO | 2012075286 A2 | 6/2012 |
| WO | 2012110010 A1 | 8/2012 |
| WO | 2012116290 A2 | 8/2012 |
| WO | 2013036835 A1 | 3/2013 |
| WO | 2013043985 A1 | 3/2013 |
| WO | 2013056181 A1 | 4/2013 |
| WO | 2013112605 A2 | 8/2013 |
| WO | 2013188792 A2 | 12/2013 |
| WO | 2014028398 A2 | 2/2014 |
| WO | 2014031792 A2 | 2/2014 |
| WO | 2014085668 A1 | 6/2014 |
| WO | 2014100228 A1 | 6/2014 |
| WO | 2014108808 A2 | 7/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016040322 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016127170 A1 | 8/2016 |
| WO | 2016134301 A1 | 8/2016 |
| WO | 2016164763 A1 | 10/2016 |
| WO | 2016205721 A1 | 12/2016 |
| WO | 2017021325 A1 | 2/2017 |
| WO | 2017066240 A1 | 4/2017 |
| WO | 2017087864 A1 | 5/2017 |
| WO | 2017156103 A1 | 9/2017 |
| WO | 2018013613 A1 | 1/2018 |
| WO | 2018013615 A1 | 1/2018 |
| WO | 2018035095 A1 | 2/2018 |
| WO | 2018039378 A1 | 3/2018 |
| WO | 2018048789 A1 | 3/2018 |
| WO | 2018169798 A1 | 9/2018 |
| WO | 2018195186 A1 | 10/2018 |
| WO | 2018236955 A1 | 12/2018 |
| WO | 2018237282 A1 | 12/2018 |
| WO | 2019/051477 A1 | 3/2019 |
| WO | 2019/055764 A1 | 3/2019 |
| WO | 2019051264 A1 | 3/2019 |
| WO | 2019094724 A1 | 5/2019 |
| WO | 2019/113494 A1 | 6/2019 |
| WO | 2019/126741 A1 | 6/2019 |
| WO | 2019/126761 A1 | 6/2019 |
| WO | 2019/140272 A1 | 7/2019 |
| WO | 2019/241442 A1 | 12/2019 |
| WO | 2020/077255 A1 | 4/2020 |
| WO | 2020/082065 A1 | 4/2020 |
| WO | 2020/118060 A1 | 6/2020 |
| WO | 2020/132504 A1 | 6/2020 |
| WO | 2020/243027 A1 | 12/2020 |
| WO | 2020/243488 A1 | 12/2020 |
| WO | 2020264495 A1 | 12/2020 |
| WO | 2020264509 A1 | 12/2020 |
| WO | 2020264512 A1 | 12/2020 |
| WO | 2021/113786 A1 | 6/2021 |

(56) References Cited

FOREIGN PATENT DOCUMENTS

| | | |
|---|---|---|
| WO | 2021/188778 A2 | 9/2021 |
| WO | 2021/195297 A1 | 9/2021 |
| WO | 2021/195301 A1 | 9/2021 |
| WO | 2021262836 A1 | 12/2021 |
| WO | 2022/020363 A1 | 1/2022 |
| WO | 2022/020363 A9 | 3/2022 |
| WO | 2022020363 A9 | 3/2022 |
| WO | 2022115381 A1 | 6/2022 |
| WO | 2022165017 A1 | 8/2022 |
| WO | 2022177718 A1 | 8/2022 |
| WO | 2022197901 A1 | 9/2022 |
| WO | 2022221195 A1 | 10/2022 |
| WO | 2022232494 A1 | 11/2022 |
| WO | 2022232504 A1 | 11/2022 |
| WO | 2023158668 A1 | 8/2023 |
| WO | 2023163879 A1 | 8/2023 |

OTHER PUBLICATIONS

Martini et al., "Nasal and pulmonary drug delivery systems", Exp. Opin. Ther. Patents, (2000), 10(3):315-323.
Marx et al., "Neuroactive steroids are altered in schizophrenia and bipolar disorder: relevance to pathophysiology and therapeutics", Neuropsychopharmacology (2006) 31, 1249-1263.
Matsumoto et al., "GAGAä receptor neutrotransmission dysfunction in a mouse model of social isolation-induced stress: Possible insights into a non-serotonergic mechanism of action of SSRIs in mood and anxiety disorders", Stress, Mar. 2007; 10(1): 3-12.
Mayer et al., "Refractory Status Epilepticus Frequency, Risk Factors, and Impact on Outcome", Archives of Neurology (2002), vol. 59, pp. 205-210.
Meierkord et al., "EFNS Guideline on the Management of Status Epilepticus in Adults", European Journal of Neurology (2010), vol. 17, pp. 348-355.
Meltzer-Brody et al., "Phase 2 and 3 Studies Evaluating Brexanolone iv, a GABAA Receptor Positive Allosteric Modulator, in Postpartum Depression", Presented at the 56th Annual Meeting of the American College of Neuropsychopharmacology; Dec. 3, 2017, 14 pages.
Melville, "New drug shows rapid, robust effect in postpartum", Medscape, (2017), 2 pages.
Merzlikine et al., "Development of machine learning models of b-cyclodextrin and sulfobutylether-b-cyclodextrin complexation free energies", International Journal of Pharmaceutics (2011), vol. 418, pp. 207-216.
Miller, "Postpartum Depression", Clinician's Corner, vol. 287, No. 6, (2002), pp. 762-765.
Monagle et al., "A Phase 1c Trial Comparing the Efficacy and Safety of a New Aqueous Formulation of Alphaxalone with Propofol", Anesthesia & Analgesia (2015), vol. 121, No. 4, pp. 914-924.
Morgan, et al. "Neuroactive steroids after estrogen exposure in depressed postmenopausal women treated with sertraline and asymptomatic postmenopausal woman", Arch Womens Ment, Health (2010) 13:91-98.
Moses Kolko et al., "Antepartum and Postpartum Depression: Healthy Mom, Healthy Baby", Journal of the American Medical Women's Association, 2004; 59: pp. 181-191.
Munari et al., "The Use of Althesin in Drug-Resistant Status Epilepticus", Epilepsia (1979), vol. 20, pp. 475-484.
Murayama et al., "Effects of neurosteroid 3a-hydroxy-5a-pregnan-20-one on ethanol-mediated paired-pulse depression of population spikes in the CA1 region of rat hippocampal slices", Neuroscience Letters 394 (2006) 28-32.
Murray et al., "Maternal Postnatal Depression and the Development of Depression in Offspring Up to 16 Years of Age", Journal of the American Academy of Child & Adolescent Psychiatry, 2011; 50 (5), pp. 460-470.
Murray et al., "Prediction, detection, and treatment of post natal depression", Archives Of Disease In Childhood, The Journal of the Royal College of Paediatrics and Child Health, 1997, 77: 97-101.

Masson et al., "Cyclodextrins and the liquid-liquid phase distribution of progesterone, estrone and prednicarbate", J Incl Phenom Macrocycl Chem (2007), vol. 57, pp. 481-487.
Naert, et al. "Neuroactive steroids modulate HPA axis actiity and cerebral brain-derived neurotrophic factor (BDNF) protein levels in adult male rats", Psychoneuroendocrinology (2007) 32, 1062-1078.
Nanjwade et al., Pulmonary Drug Delivery: Novel Pharmaceutical Technologies Breathe New Life into the Lungs, PDA JPharm Sci and Tech, (2015), 65: 513-534.
Nappi et al., "Serum Allopregnanolone in women with postpartum blues", Obstetrics & Gynecology, vol. 97, No. 1, 2001: 77-80.
Nin et al. "Neurosteroids reduce social insolation-induced behavioral deficits; a proposed link with neurosteroid-mediated upregulation of BDNF expression", Frontiers in Endocrinology (2011) vol. 2, Article 73.
Nin et al., "The effect of intra-nucleus accumbens administration of allopregnanolone on 6 and y2 GABAA receptor subunit mRNA expression in the hippocampus and on depressive-like and grooming behaviors in rats," Pharmacology, Biochemistry and Behavior, (2012), 103:359-366.
Northdurfter et al., "Recent Developments in Potential Anxiolytic Agents Targeting GABAA/BzR Complex or the Translocator Protein (18kDa) (TSPO)", Current Topics in Medicinal Chemistry, 2012, 12; 360-370.
Notification of Transmittal of the International Search Report and the Written Opinion of the International Searching authority, or the Declaration, International Application No. PCT/US13/45933, Dec. 3, 2013, 5 Pages.
Novy et al., "Refractory Status Epilepticus: A Prospective Observational Study", Epilepsia (2010), vol. 51, No. 2, pp. 251-256.
Oka et al., "A reliable method for intratracheal instillation of materials to the entire lung in rats," J Toxicol Pathol, (2006), 19:107-109.
Osborne et al., "Replication of epigenetic postpartum depression biomarkers and variation with hormone levels," Neuropsychopharmacology, Accepted Manuscript (2015), pp. 1-32.
Park et al., "Multiple effects of allopregnanolone on GABAergic responses in single hippocampal CA3 pyramidal neurons", European Journal of Pharmacology (2011), vol. 652, pp. 46-54.
Parizek et al., "Steroid hormones in the development of postpartum depression". Physiological Research, 2014, vol. 63, No. Suppl. 2, pp. S277-S282.
Pearlstein, et al. "Premenstrual dysphoric disorder: burden of illness and treatment update", J Psychiatry Neurosci 2008:33(4):291-301.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Pieribone et al., "Clinical Evaluation of Ganaxolone in Pediatric and Adolescent Patients with Refractory Epilepsy", Epilepsia (2007), vol. 48, No. 10, pp. 1870-1874.
Pinna, et al., "Up-Regulation of Neutrosteriod Biosynthesis as a Pharmacological Strategy to improve behavioural Deficits in a Putative mouse model of Post-traumatic stress disorder", Journal of Neuroendocrinology 24 (2011), p. 102-116.
Pires et al., "Intranasal Drug Delivery: How, Why and What for?" Journal of Pharm, Pharmaceut Sci, (2009), 12(3):288-311.
Poromaa et al., "GABA receptor, progresteron and premenstrual dysphoric disorder", Arch Womens Ment Health (2003) 6:23-41.
Pubchem, CID 92786.
Puia, et al. "Novel modulatory effects of neurosteriods and benzodiazepines on excitatory and inhibitory neurons excitability: a multi-electrode array recording study", Frontiers in Neutral Circuits, (2012) vol. 6, Article 94.
Ramsay, "Treatment of status epilepticus", Epilepsia, 2013, 34 Suppl.:S71-S81.
Rapkin et al., "Progesterone metabolite allopregnanolone in women with premenstrual syndrome", Obstet. Gynecol 1997; 90:709-714.
Rasmusson, et al. "Decreased Cerebrospinal Fluid Allopregnanolone levels in women with posttraumatic stress disorder", Biol. Psychiatry 2006;60:704-713.

(56) References Cited

OTHER PUBLICATIONS

Reddy "Role of anticonvulsant and antiepileptogenic neurosteroids in the pathophysiology and treatment of epilepsy," Frontiers in Endocrinology, 2:38, (2011).
Reddy "The clinical potentials of endogenous neurosteroids" Drugs of Today 2002, 38 (7): 465-485.
Reddy et al., "Neurosteroids—Endogenous Regulators of Seizure Susceptibility and Role in Treatment of Epilepsy", Jasper's Basic Mechanisms of the Epilepsies Fourth Edition (2012), pp. 1-23.
Reddy, "Neurosteroids: Endogenous role in the human brain and therapeutic potentials", Progress in Brain Research, (2010) vol. 186, pp. 113-137.
Reddy, "Pharmacology of Endogenous Neuroactive Steroids", Critical Reviews in Neurobiology, 15 (3&4)197-234 (2003).
Reddy, "SGE-102: a novel therapy for refractory status epilepticus", Epilepsia, Abstract 34 Suppl 6: 81-82.
Rogawski et al., "Neuroactive Steroids for the Treatment of Status Epilepticus", Epilepsia (2013), vol. 54, No. 6, pp. 93-98.
Romeo, et al. "Effect of antidepressant treatment on neuroactive steroids in major deprssion" Am. J. Psychiatry 1998; 155:910-913.
Rosenthal et al., "Brexanolone as adjunctive therapy in super-refractory status epilepticus," Annals of Neurology, John Wiley & Sons, (2017), 32pp.
Rossetti et al., "A Randomized Trial for the Treatment of Refractory Status Epilepticus", Neurocritical Care Society (2011), vol. 14, No. 1, pp. 4-10.
Rouge-Pont et al., "The neurosteroid allopregnanolone increases dopamine release and dopaminergic response to morphine in the rat nucleus accumbens", European Journal of Neuroscience, vol. 16, pp. 169-173, 2002.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Rupprecht et al.. "Neuroactive steroids; mechanisms of action and neuropsychopharmacological perspectives", Trends Neurosci. (1999) 22, 410-416.
Saady et al., "Case Report: Althesin in Status Epilepticus" Aneasth. Intens. Care (1979), vol. 7, No. 3, pp. 267-270.
Saalmann et al., "Neurosteroids involved in regulating inhibition in the inferior colliculus" J. Neurophysiol 96: 3064-3073, 2006.
Sahin et al., "Outcome of Severe Refractory Status Epilepticus in Children", Epilepsia (2001), vol. 41, No. 11, pp. 1461-1467.
Sanborn et al., "Identifying and managing adverse environmental health effects: 4. Pesticides, " CMAJ, (2002) 166(11):1431-1436.
Santoru et al., "Decreased allopregnanolone induced by hormonal contraceptives is associated with a reduction in social behavior and sexual motivation in female rats," Psychopharmacology, (2014), 14pp.
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Schiller et al., "Allopregnanolone as a mediator of affective switching in reproductive mood disorders," Psychopharmacology, (2014), 11pp.
Schiller et al., "The role of reproductive hormones in postpartum depression," CNS Spectrums, (2015), 20(1):48-59.
Schule et al., "Neuroactive steriods in Affective Disorders: target for Novel antidepressant or anxiolytic drugs", Neuroscience 191 (2011) p. 55-77.
Schule et al., "The role of allopregnanolone in depression and anxiety", Progress in Neurobiology 113 (2014) 79-87.
Shah et al., "Peripheral WBC Count and Serum Prolactin Level in Various Seizure Types and Nonepileptic Events", Epilepsia (2011), vol. 42, No. 11, pp. 1472-1475.
Shimizu et al., "Allopregnanolone increases mature excitatory synapses along dendrites via protein kinase A signaling ," Neuroscience, (2015), 305:139-145.
Shorvon et al., "The Outcome of Therapies in Refractory and Super-Refractory Convulsive Status Epilepticus and Recommendations for Therapy", Brain (2012), vol. 135, No. 8, pp. 2314-2328.
Shorvon et al., "The Proceedings of the First London Colloquium on Status Epilepticus", University College London, Apr. 12-15 , Epilepsia (2007), vol. 48, No., 8, pp. 1-3.
Shorvon et al., "The Treatment of Super-Refractory Status Epilepticus: A Critical Review of Available Therapies and a Clinical Treatment Protocol", Brain (2011,) vol. 134, No. 10, pp. 2802-2818.
Shu et al., "Characteristics of concatemeric GABM receptors containing alpha4/d subunits expressed in Xenopus pocytes" British Journal of Phannacology (2012) 165, 2228-2243.
Smith et al., "The influence of stress at puberty on mood and learning: Role of the a4136 GABAA receptor," Neuroscience, (2013), 249:192-213.
Stevens et al., "Hormonal Therapy for Epilepsy", Curr Neurol. Neurosci Rep. 11: 2011, pp. 435-442.
Supplemental European Search Report, European Patent Application No. 14826212.4, mailed Feb. 16, 2017.
Timby et al., "Pharmacokinetic and behavioral effects of allopregnanolone in healthy women", Psycopharmacology (2006), vol. 186, pp. 414-424.
Timby et al., "Women with premenstrual dysphoric disorder have altered sensitivity to allopregnanolone over the menstrual cycle compared to controls-a pilot study," Psychopharmacology, (2016), 233:2109-2117.
Tolmacheva et al., "The role of ovarian steroid hormones in the regulation of basal and stress induced absence seizures", Journal of Steroid Biochemistry & Molecular Biology (2007), vol. 104, pp. 281-288.
Tongiani et al., "Sulfobutyl Ether-Alkyl Ether Mixed Cyclodextrin Derivatives With Enhanced Inclusion Ability", Journal of Pharmaceutical Sciences (2009), vol. 98, No. 12, pp. 4769-4780.
Turkmen et al., "Tolerance to Allopregnanolone with Focus on the GABA-A Receptor", British Journal of Pharmacology (2011), vol. 162, pp. 311-327.
Ueda et al., "Evaluation of a Sulfobutyl Ether b-Cyclodextrin as a Aolubilizing/Stabilizing Agent for Several Drugs", Drug Development and Industrial Pharmacy (2008), vol. 24, No. 9, pp. 863-867.
Ungard et al., "Modification of behavioral effects of drugs in mice by neuroactive steroids", Psychopharmacology (2000) 148:336-343.
Upasani et al., "3a-Hydroxy-3B-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.
Uzunova et al. "Region-specific dysregulation of allopregnanolone brain contante tin the olfactory bulbectomized rat model of depression", Brain Research 976 (2003) 1-8.
Uzunova et al., "Relevance of endogenous 3a-reduced neurosteroids to depression and antidepressant action", Psycopharmacology (2006) 186: 351-361.
Vaitkevicius et al., "First-in-man allopregnanolone use in super-refractory stats epilepticus", Annals of Clinical and Translational Neurology, vol. 4, No. 6, 2017, pp. 411-414.
Vaitkevicius et al., "Successful allopregnanolone treatment of new onset refractory status epilepticus (Norse) syndrome: First in man experience," Epilepsia, (2013), Abstract p. 114.
Van Broekhoven et al., "Neurosteroids in depression: a review", Psychopharmacology (2003) 165:97-110.
Vanlandingham et al., "Progesterone and its metabolite allopregnanolone differentially regulate hemostatic proteins after traumatic brain injury", Journal of Cerebral Blood Flow & Metabolism (2008), vol. 28, pp. 1786-1794.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a

(56) References Cited

OTHER PUBLICATIONS

Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Vine et al., "2H-Labelled 3a-Hydroxy-5a-Pregnane-11, 20-Dione and 3a, 21-Dihydroxy-5a-Pregnane-11, 20-Dione 21-Acetate", Journal of Labelled Compounds and Radiopharmaceuticals, vol. IX, No. 4, 1982, pp. 597-604.
Weisberg et al., "Seizure disorders," Essentials of Clinical Neurology, Chapter 11, (1983), pp. 167-175.
Wirth, "Beyond the HPA axis; progesterone-derived neuroactive steroids in human stress and emotion," Frontiers in Endocrinology (2011) vol. 2, Article 19.
Wolkowitz, et al. "Of Sound Mind and Body; depression, disease, and accelerated aging", Dialogues in Clinical Neuroscience, vol. 13, No. 1, 2011, p. 25-39.
Yunes et al., "Postnatal administration of allopregnanolone modifies glutamate release but not BDNF content in striatum samples of rats prenatally exposed to ethanol", Biomed Research International, vol. 2015, 2015, pp. 1-6.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zia et al., "Effect of Alkyl Chain and Degree of Substitution on the Complexation of Sulfoalkyl Ether b-Cyclodextrins with Steroids", Journal of Pharmaceutical Sciences (1996), vol. 86, No. 2, pp. 220-224.
Zia et al., "Effect of Cyclodextrin Charge on Complexation of Neutral and Charged Substrates: Comparison of (SBE) 7M-b-CD to HP-b-CD", Pharmaceutical Research (2001) vol. 18, No. 5, pp. 667-673.
Zia et al., "Thermodynamics of Binding of Neutral Molecules to Sulfobutyl Ether b-Cyclodextrins (SBE-b-CDs): The Effect of Total Degree of Substitution", Pharmaceutical Research (2000), vol. 17, No. 8, pp. 936-941.
International Search Report and Written Opinion for corresponding International Application No. PCT/US2013/22772 dated Mar. 27, 2013.
International Search Report and Written Opinion for corresponding International Application No. PCT/US2013/56062 dated Jan. 29, 2014.
International Search Report and Written Opinion for corresponding International Application No. PCT/US2015/48937 dated Feb. 5, 2016.
International Search Report and Written Opinion for Corresponding International Application No. PCT/US2016/018748 dated Aug. 29, 2016.
International Search Report and Written Opinion for corresponding International Application No. PCT/US2016/026705 dated Aug. 19, 2016.
International Search Report and Written Opinion for corresponding International Application No. PCT/US2016/038195 dated Oct. 20, 2016.
International Search Report and Written Opinion for corresponding International Application No. PCT/US2017/021325 dated May 22, 2017.
International Search Report and Written Opinion for corresponding International Application No. PCT/US2018/050444 dated Dec. 3, 2018.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, mailed Jan. 22, 2015.
International Search Report for International Application No. PCT/US2012/060136 dated Mar. 27, 2013.
Irwin et al., "Allopregnanolone preclinical acute pharmacokinetic and pharmacodynamic studies to predict tolerability and efficacy for alzheimer's disease", Plos One, vol. 10, No. 6, 2015, pp. 1-31.
Jain et al., "Hygroscopicity, phase solubility and dissolution of various substituted sulfobutylether b-cyclodextrins (SBE) and danazol-SBE inclusion complexes", International Journal of Pharmaceutics (2001), vol. 212, pp. 177-186.
Jin et al., "A sensitive and selective LC-differential mobility-mass spectrometric analysis of allopregnanolone and pregnanolone in human plasma", Analytical and Bioanalytical Chemistry, vol. 405, No. 29, 2013, pp. 1-23.
Johnson et al., "Deuterium Labelled Steroid Hormones: Syntheses and Applications in Quantitation and Endocrinology", Journal of Steroid Biochemistry, vol. 14, 1981, pp. 793-800.
Jones, "Post-partum depression—a glimpse of light in the darkness?", Published online Jun. 12, 2017, 2 pages.
Kaminski et al., "Allopregnanolone analogs that positively modulate GABAA receptors protect against partial seizures Induced by 6-Hz electrical stimulation in mice," Epilepsia, (2004), 45(7):864-867.
Kanes et al., "Brexanolone (SAGE-547 injection) in post partum depression: a randomised controlled trial", The Lancet, 2017; vol. 390, Issue 10093, pp. 480-489.
Kanes et al., "Open-label, proof-of-concept study of brexanolone in the treatment of severe postpartum depression", Hum Psychopharmacol Clin Exp. (2017).
Kanto, "Midazolam: The first water-soluble benzodiazepine pharmacology, pharmacokinetics and efficacy in insomnia and anesthesia", Pharmacotherapy, (1985), 5(3): 138-155.
Kask et al., "Allopregnanolone has No. effect on startle response and prepulse inhibition of startle response in patients with premenstrual dysphoric disorder or healthy controls", Pharmacology, Biochemistry and Behavior (2009), vol. 92, pp. 608-613.
Kask et al., "Allopregnanolone impairs episodic memory in healthy women", Psycopharmacology (2008), vol. 199, pp. 161-168.
Kaura et al., "The Progesterone metabolite allopregnanolone potentiates GABAA rceptor-mediated inhibition of 5-HT neuronal activity", European Neuropsychopharmacology, (2007), 17, pp. 108-115.
Khanna et al., "Nanotoxicity: An interplay of oxidative stress, inflammation and cell death," nanomaterials, (2015), 5:1163-1180.
Khisti et al., "Serotonergic agents modulate anti-depressant-like effect of the neurosteroid 3a-hydroxy-5a-pregnan-20-one in mice" Brain Research 865 (2000) 291-300.
Kim et al., "Modulation of presynaptic GABAA receptors by endogenous neurosteroids", British Journal of Pharmacology (2011), vol. 164, pp. 1698-1710.
Kimmel et al., "Oxytocin receptor DNA methylation inpostpartum depression," Psychoneuroendocrinology, (2016), 69:150-160.
Klatzkin et al. "Associations of histories of depression and PMDD diagnosis with allopregnanolone concentrations following the oral administration of micronized progesterone", Psychoneuroendocrinology (2006) 31, 1208-1219.
Klatzkin et al., "Histories of depression, allopregnanolone responses to stress, and premenstrual symptoms in women:", Biological Psychology 71 (2006) 2-11.
Kokate et al., "Anticonvulsant Activity of Neurosteroids: Correlation with g-Aminobutyric Acid-Evoked Chloride Current Potentia-

(56) References Cited

OTHER PUBLICATIONS tion", The Journal of Pharmacology and Experimental Therapeutics (1994), vol. 270, No. 3, pp. 1223-1229.
Kokate et al., "Convulsant actions of the neurosteroid pregnenolone sulfate in mice", Brain Research (1999), vol. 831, pp. 119-124.
Kokate et al., "Neuroactive Steroids Protect Against Pilocarpine- and Kainic Acid-induced Limbic Seizures and Status Epilepticus in Mice", Neuropharmacology (1996) vol. 35, No. 8, pp. 1049-1056.
Kramer, "Early Ketamine to Treat Refractory Status Epilepticus" Neurocrit. Care (2012), vol. 16, pp. 299-305.
Kushner et al., "Pharmacological uses and perspectives of heavy water and deuterated compounds". Candian Journal Physiology and Pharmacology, vol. 77, pp. 79-88 (1999).
Lahiani-Skiba et al., "Solubility and Dissolution Rate of Progesterone- Cyclodextrin-Polymer Systems", Drug Development and Industrial Pharmacy (2006), vol. 32, pp. 1043-1058.
Larsen et al., "Phase Solubility and Structure of the Inclusion Complexes of Prednisolone and 6a-Methyl Prednisolone with Various Cyclodextrins", Journal of Pharmaceutical Sciences (2005), vol. 94, No. 3, pp. 507-515.
Leroy et al., "Pharmacological plasticity of GABAA receptors at dentate gyrus synapses in a rat model of temporal lobe epilepsy", J. Physol. (2004), vol. 557, No. 2, pp. 473-487.
Li et al., "Nanoparticle-induced pulmonary toxicity," Experimental Biology and Medicine, (2010), 235:1025-1033.
Lonsdale et al., "The Anticonvulsant effects of allopregnanolone against amygdala-kindled seizures in female rats", Neuroscience Letters (2007), vol. 411, pp. 147-151.
Lossin et al., "Allopregnanolone treatment in a rat pediatric status epilepticus model: Comparison with diazepam", American Epilepsy Society (2012), (Abst. 3.220).
MacKenzie et al., "Neurosteriods and GABAergic signaling in health and disease", BioMol Concepts 2013; 4(1): 29-42.
Madl et al., "Nanoparticles, lung injury, and the role of oxidant stress," Annu Rev Physiol., (2014), 76:447-465.
Maguire et al., "GABAAR plasticity during pregnancy relevance to postpartum Depression," Neuron, (2008), 59:207-213.
Eser et al., "Neuropsychopharmacological properties of neuroactive steroids in depression and anxiety disorders", Psychopharmacolody, (2006) 186: pp. 373-387.
Evans, et al. "Allopregnanolone regulates neurogensis and depressive/ anxiety-like behaviour in social isolation rodent model of chronic stress", Neuropharmacology 63 (2012) 1315-1326.
Extended European Search Report for application PCT/ CN2014075593 dated Aug. 26, 2016.
Extended European Search Report for application PCT/ CN2014075594 dated Aug. 26, 2016.
Extended European Search Report for European Application No. 13740743.3 dated Jan. 14, 2016.
Extended European Search Report for European Application No. 13830765.7 dated Jan. 12, 2016.
Extended European Search Report for European Application No. 13857993.3 dated May 2, 2016.
Finn et al., "The Estrus Cycle, Sensitivity to Convulsants and the Anticonvulsant Effect of Neuroactive Steroid", The Journal of Pharmacology and Experimental Therapeutics (1994), vol. 271, pp. 164-170.
Fitelson et al., "Treatment of postpartum despression: clinical, psychological and pharmacological options", International Journal of Women's Health, 2011, pp. 1-14.
Foster, "Deuterium isotope effects in studies of drug metablosim". Trends in Pharmacological Sciences, vol. 5, pp. 524-527 (Abstract) (1984).
Frank et al., "Neuroprotective effects of allopregnenolone on hippocampal irreversible neurotoxicity in vitro", Prog. Neuropsychopharmacol. & Biol Psychiat. 2000, vol. 24, pp. 1117-1126.
Freeman et al., "Allopregnanolone levels and symptom improvement in severe premenstrual syndrome", J. Clin. Psychopharmacol 2002; 22:516-520.

Frye et al. "Hippocampal 3a,5a-THP may alter depressive behavior of pregnant an lactating rats", Pharmacology, Biochemistry and Behavior 78 (2004) 531-540.
Frye et al., "Changes in Progesterone metabolites in the hippocampus can modulate open field and forced swim test behavior of proestrous rats", Hormones and Behavior 41, 306-315 (2002).
Frye et al., "Infusion of 3a,5a-THP to the pontine reticular formation attenuates PTZ-induced seizures", Brain Research (2000), vol. 881, pp. 98-102.
Frye, "The neurosteroid 3-a, 5 a-THP has antiseizure and possible neuroprotective effects in an animal model of epilepsy," Brain Research, (1995), 696:113-120.
Frye, et al., "Effects and mechanism of 3a,5a,-THP on emotion, motivation, and reward functions involving pregnane kenobiotic receptor", Frontiers in Neuroscience (2012), vol. 5, Article 136, pp. 1-18.
Galvin et al., "Midazolam: an effective intravenous agent for seizure control," Archives of emergency medicine, (1987), 4:169-172.
Gasior et al., "Anticonvulsant and behaviorial effects of neuroactive steroids alone and in conjunction with diazepam", The Journal of Pharmacology and Experimental Therapeutics (1997), vol. 282, No. 2, pp. 543-553.
Gasior et al., "Neuroactive steroids: potential therapeutic use in neurological and psychiatric disorders", Trends in Pharmacological Science, (1999), vol. 20, No. 3, pp. 107-112.
Gaynes et al., "Perinatal Depression: Prevalence, Screening Accuracy, and Screening Outcomes", Evidence Report/Technology Assessment, (2005), No. 119, pp. 1-8.
Gilbert et al., "3a-reduced neuroactive steroids and their precursors during pregnancy and the postpartum period", Gynecol Endocrinol., (2005), 21(5): pp. 268-279.
Girdler et al. "Neurosteroids in the context of stress: Implications for depressive disorders", Pharmacology & Therapeutics 116 (2007) 125-139.
Griffin et al., "Current perspectives on the role of neurosteroids in PMS and depression", International Review of Neurobiology, vol. 46, 2001, pp. 479-492.
Guidotti et al., "The socially-isolated mouse: a model to study the putative role of allopregnanolone and 5a-dihydroprogesterone in psychiatric disorders", Brain Research Reviews 37 (2001) 110-115.
Gul et al., "Sterols and the phytosterol content in oilseed rape (*Brassica napus* L.)", Journal of Cell and Molecular Biology (2006), 5: 71-79.
Haas et al., "Ketamine: A Review of Its Pharmacologic Properties and Use in Ambulatory Anesthesia", Anesthesia, Anesthesia Progress, The American Dental Society of Anesthesiology (1992), vol. 39, pp. 61-68.
Hanley et al., "Use of midazolam in the treatment of refractory status epilepticus", Clinical Therapeutics, (1998), 20(6): 1093-1105.
Hardoy et al. "The link between neurosteroids and syndromic/ syndromal components of the mood spectrum disorders in women during the premenstrual phase", Clinical Practice and Epidemiology in Mental Health 2008, 4:3.
Hardoy, et al., "Increased neuroactive steroids concentrations in women with bipolar disorder or major depressive disorder", J. Clin Psychopharmacol 2006;26:379-384.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Haut et al., "Seizure clustering during epilepsy monitoring", Epilepsia, (2002), 43(7): 711-715.
Haut, "Seizure clustering", Epilepsy & Behavior, (2006), 8:50-55.
Haut, "Seizure Clusters: characteristics and treatment," Current Opin. Neurol., (2015), 28(2):143-150, Abstract only.
Hawkinson et al., "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.
Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

(56) References Cited

OTHER PUBLICATIONS

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

Hay et al., "Pathways to Violence in the Children of Mothers Who Were Depressed Postpartum", Developmental Psychology, 2003, vol. 39, No. 6, pp. 1083-1094.

He J et al., "Allopregnanolone facilitates spatial learning after traumatic brain injury", Abstracts of the Annual Meeting of the Society for Neuroscience (2000) p. 2296.

Hellgren et al., "Low serum allopregnanolone is associated with symptoms of depression in late pregnancy," Neuropsychobiology, (2014), 69:147-153.

Hincal, "Recent advances in drug delivery using amphiphilic cyclodextrin nanoparticles", European Journal of Pharmaceutical Sciences (2005), vol. 23S1, pp. S3-S4.

Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.

Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.

Huber, et al. "Effect of an oral contrceptive with chlormadinone Acetate on depressive mood", Clin Drug Invest 2008: 28 (12): 783-791.

Hunter et al., "Status Epilepticus: A Review, With Emphasis on Refractory Cases" Can. J. Neurol. Sci. (2012), vol. 39, pp. 157-169.

International Search Report and Written Opinion (Declaration of non-establishment of International Search Report) for corresponding International Application No. PCT/US2011/062888 dated Jun. 15, 2012.

International Search Report and Written Opinion for corresponding International Application No. PCT/US13/56062 dated Jan. 29, 2014.

International Search Report and Written Opinion for corresponding International Application No. PCT/US2012/056509 dated Dec. 27, 2012.

International Search Report and Written Opinion for corresponding International Application No. PCT/US2013/054562 dated Jan. 13, 2014.

International Search Report and Written Opinion for corresponding International Application No. PCT/US2013/072351 dated Mar. 17, 2014.

"Allopregnanolone for the Treatment of Traumatic Brain Injury" ClinicalTrials.gov, Updated May 22, 2013, pp. 1-4.

"Sage Therapeutics Announces Brexalone Achieves Primary Endpoints in Both Phase 3 Clinical Trials in Postpartum Depression", Press Release, Nov. 9, 2017.

"Sage Therapeutics Welcome to R&D day 2016", Jan. 1, 2016, pp. 1-143.

"Sage Therapeutics Wins Big in Depression Trial", Press Release, 247Chrislange, Nov. 9, 2017.

Abend et al., "Treatment of refratory status epilepticus: Literature review and a proposed protocol", Pediatric Neurology, vol. 38, No. 6, 2008, pp. 377-390.

Akhondzadeh et al., "Induction of a novel form of hippocampal long-term depression by muscimol: involvement of GABAA but not glutamate receptors", British Journal of Pharmacology (1995) 115, 527-533.

Aladdin et al., "Refractory Status Epilepticus During Pregnancy Secondary to Cavernous Angiona", Epilepsia, vol. 49, No. 9, (2008), pp. 1627-1629.

Allen et al., "Menstrual phase, depressive symptoms, and allopregnanolone during short-term smoking cessation," Experimental and Clinical Psychopharmacology, (2013) 21(6):427-433.

Amin et al., "The interaction of neuroactive steroids and GABA in the development of neuropsychiatric disorders in women", Pharmacology, Biochemistry and Behavior 84 (2006) 635-643.

Anderson et al., "Oxidative/nitrosative stress and immunoinflammatory pathways in depression: Treatment Implications," Current Pharmaceutical Design, (2014) 20(25):4126-4161.

Anovadiya et al., "Epilepsy: Novel Therapeutic Targets", Journal of Pharmacology and Pharmacotherapeutics, 2012, pp. 112-117.

Backstrom et al. "Pathogensis in Menstrual cycle-linked CNS disorders", Ann. N.Y. Acad. Sci. 1007: 42-53 (2003).

Baker et al., "Efficacy of progesterone vaginal suppositories in Alleviation of Nervous Symptoms in Patients with Premenstrual Syndrome", Journal of Assisted Reproduction and Genetics, vol. 12, No. 3 1995, pp. 205-209.

Bali, et al. Multifunctional aspects of allopregnanolone in stress and related disorders, Progress in Neuro-Psychopharmacology & Biological Psychiatry 48 (2014) 64-78.

Bancaud et al., (From the Commission on Classification and Terminology of the International League Against Epilepsy) (Aug. 1981) "Proposal for Revised Clinical and Electroencephalographic Classification of Epileptic Seizures," Epilepsia, 22:489-501.

Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).

Beckley et al., "Progesterone receptor antagonist CDB-4124 increases depression-like behavior in mice without affecting locomotor ability," Psychoneuroendocrinology, (2011) 36:824-833.

Bernardi, et al., "Disadaptive disorders in women: allopregnanolone, a sensitive steroid", Gynecol Endocrinol 2004; 19:344-353.

Biagini et al., "Endogenous neurosteroids modulate epileptogenesis in a model of temporal lobe epilepsy", Experimental Neurology, (2006), vol. 201, pp. 519-524.

Bicikova et al., "Serum concentrations of some neuroactive steroids in women suffering from mixed anxiety-depressive disorder", Neurochemical Research, vol. 25, No. 12, 2000, pp. 1623-1627.

Birzniece et al., "Neuroactive steroid effects of cognitive functions with a focus on the serotonin and GABA systems" Brain Research Reviews 51 (2006) 212-239.

Bleck et al., "Refractory Status Epileptics", Current Opinion in Critical Care, (2005), vol. 11, pp. 117-120.

Bobb et al., "Allopregnanolone to treat refractory status epilepticus," presented at American Clinical Neurophysiology, Society (ACNS) Annual Meeting & Courses, The Westin Peachtree Plaza, Atlanta, Georgia, (Feb. 4-9, 2014) Abstract S26.

Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.

Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.

Broomall et al., "Pediatric super-refractory status epilipticus treated with allopregnanolone," Ann. Neurol, (2014), 76: 911-915.

Brown et al., "A randomized, double-blind, placebo-controlled trial of pregnenolone for bipolar depression," Neuropsychopharmacology, (2014) 39:2867-2873.

Brunn et al., "Combined treatment with diazepam and allopregnanolone reverses tetramethylenedisulfotetramine (TETS)-induced calcium dysregulation in cultured neurons and protects TETS-intoxicated mice against lethal seizures," Neuropharmacology, (2015), 95:332-342.

Burdock, "Encyclopedia of food additives and coloring," Taylor & Francis, 3 Volume Set, (1997), pp. 2410-2413.

Cao et al., "Tetramethylenedisulfotetramine alters Ca2+ dynamics in cultured hippocampal neurons: Mitigation by NMDA receptor blockade and GABAA receptor-positive modulation," Toxicological Sciences, (2012), 130(2):362-372.

Carta, et al. "GABAergic neuroactive steroids: a new frontier in bipolar disorders", Behavioral and Brain Functions 2012, 8:61.

(56) References Cited

OTHER PUBLICATIONS

Chen et al., "Ibogaine block of the NMDA receptor: In vitro and in vivo studies," Neuropharmacology, (1996) 35(4):423-431.

Chiasari et al., "The Influence of Neuroactive Steroid Lipophilicity on GABA Receptor Modulation: Evidence for a Low-Affinity Interaction", Journal of Neurophysiology (2009), vol. 102, pp. 1254-1264.

Claassen et al., "Treatment of Refractory Status Epilepticus with Pentobarbital, Propofol, or Midazolam: A Systematic Review", Epilepsia (2002), vol. 43, No. 2, pp. 146-153.

D'Aquila, et al. ."Dopamine is involved in the anti-depressant-like effect of allopregnanolone in the forced swimming test in female rats", Behavioural Pharmacology 2010, 21:21-28.

Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].

Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].

De Crescenzo et al., "Selective serotonin reuptake inhibitors (SSRIs) for post-partum depression (PPD): A systematic review of randomized clinical trials", Journal of Affective Disorders, 152-154 (2014) 39-44.

Deligianndis et al., "Peripartum neuroactive steroid and y-aminobutyric acid profiles in women at-risk for postpartum depression," Psychoneuroendocrinology, Accepted Manuscript, (2016), 33p.

Deligiannidis, et al. "GABAergic neuroactive steroids and resting-state functional connectivity in postpartum depression; A preliminary study", Journal of Psychiatric Research 47 (2013) 816-828.

Delorenzo et al., "Epidemiology of Status Epilepticus" Journal of Clinical Neurophysiology (1995), vol. 12, No. 4, pp. 316-325.

Deutsch et al., "Evaluation of In Vivo Interactions in Mice Between Flurazepam and Two Neuroactive Steroids", Pharmacology Biochemistry & Behavior (1996), vol. 55, No. 3, pp. 323-326.

Dhir et al., "Role of neurosteroids in the anticonvulsant activity of midazolam," British Journal of Pharmacology, (2012), 165(8): 2684-2691.

Dhir et al., "Seizure protection by intrapulmonary delivery of midazolam in mice," Neuropharmacology, (2013), 73:425-431.

Dhir et al., "Seizure protection by intrapulmonary delivery of propofol hemisuccinate," The Journal of Pharmacology and Experimental Therapeutics, (2011), 336(1):215-222.

Dorwald, "Side Reactions in Organic Synthesis", 2005, Wiley-VCH, Preface, p. IX.

Drugan et al. "Resilience in shock and swim stress models of depression", Frontiers in Behavorial Neuroscience, Feb. 2013, vol. 7, Article 14.

Dyck et al., "Effects of Deuterium Substitution on the Catabolism of beta-Phenylethylamine: An In Vivo Study". J. Neurochem., vol. 46(2), pp. 399-404 (1986).

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.

Eser et al., "Neuroactive Steroids in Depression and Anxiety Disorders: Clinical Studies", Neuroendocrinology, (2006) 84: pp. 244-254.

Atiemo-Obeng et al., "Rotor-Stator Mixing," Handbook of Industrial Mixing: Science and Practice, 2004, pp. 479-505.

Hancock, et al., "Ultrasonic Cleaning," ASM Handbook, vol. 5: Surface Engineering, 1994, pp. 44-47.

Zhang et al. "High shear mixers: A review of typical applications and studies on power draw, flow pattern, energy dissipation and transfer properties," Elsevier B.V.: Chemical Engineering and Processing: Process Intensification, 2012, pp. 25-41.

Del Valle, E.M., "Cyclodextrins and their uses: a review", Process Biochemistry, 2003, pp. 1-14.

Rajewski et al. J Pharm Sci. Aug. 1995;84(8): 927-32 (Year: 1995).

Rasheed et al., "Cyclodextrins as Drug Carrier Molecule: A Review", Scientia Pharmceutica, Review, (2008), pp. 567-598.

Supplementary European Search Report for International Application No. PCT/US2013/022772 dated Jan. 14, 2016.

Supplementary European Search Report for International Application No. PCT/US2013/056062 dated Jan. 12, 2016.

Zhu et al. "Evaluation and comparison of the pharmacokinetic properties of allopregnanolone and pregnanolone at inuction of anaesthesia in the male rat" British Journal of Anaesthesia (2001) vol. 86, No. 3, pp. 403-412.

5.0 mg/mL    7.5 mg/mL    9.0 mg/mL    10.0 mg/mL  ALLO

METHODS OF TREATING EPILEPSY OR STATUS EPILEPTICUS

CLAIMS OF PRIORITY

This application is a continuation of U.S. application Ser. No. 16/419,761, filed on May 22, 2019, which is a continuation of U.S. application Ser. No. 15/940,505, filed on Mar. 29, 2018, which is a continuation of U.S. application Ser. No. 13/972,851, filed on Aug. 21, 2013, which claims priority to U.S. Ser. No. 61/691,545, filed Aug. 21, 2012 and U.S. Ser. No. 61/789,491, filed Mar. 15, 2013. The entire contents of the aforementioned applications are incorporated herein by reference in their entireties.

FIELD OF THE INVENTION

The present invention generally relates to methods of treating epilepsy or status epilepticus by administering a neuroactive steroid.

SUMMARY OF THE INVENTION

Described herein are methods of treating epilepsy or status epilepticus. e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; periodic lateralized epileptiform discharges; a seizure, e.g., acute repetitive seizures, cluster seizures, the method comprising administering to the subject a neuroactive steroid. In one aspect, the invention features a method of treating a subject having epilepsy or status epilepticus by administering in combination to the subject a neuroative steroid and a benzodiazepine. In some embodiments, the method further comprises administering at least one of the neuroative steroid or benzodiazepine parenterally (e.g., intranasally, buccally, intravenously or intramuscularly, for example, intravenously or intramuscularly). In some embodiments, both the neuroative steroid and benzodiazepine are administered parenterally.

In some embodiments, the neuroative steroid and benzodiazepine are co-administered (e.g., administered simultaneously). In some embodiments, the neuroative steroid and benzodiazepine are administered sequentially. In some embodiments, neuroative steroid and benzodiazepine are administered in a single dosage form.

When the agents described herein (e.g., the neuroactive steroid and a benzodiazepine) are administered in combination, both of the agents should be present at dosage levels of between about 1 to 100%, and more preferably between about 5 to 95% of the dosage normally administered in a in the absence of the combination regimen. The agents may be administered separately, as part of a multiple dose regimen. Alternatively, the agents may be part of a single dosage form, mixed together with the compounds of this invention in a single composition.

In some embodiments, the neuroactive steroid is a progestin derivative, e.g., allopregnanolone. In an embodiment, the neuroactive steroid is allopregnanolone.

In some embodiments, the nerruoactive steroid, e.g., alloprenanolone, is formulated for parenteral administration (e.g., intranasally, buccally, intravenously or intramuscularly, for example, intravenously or intramuscularly).

In some embodiments, the neneuroactive steroid, e.g., allopregnanolone, is administered in a composition comprising a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex. a β-cyclodextrin, e.g., a sulfo butyl ether β-cyclodextrin, e.g., a β-cyclodextrin, e.g., a sulfo butyl ether β-cyclodextrin, e.g., CAPTISOL®.

In some embodiments, the cyclodextrin is a β-cyclodextrin. In an embodiment, the cyclodextrin is a sulfo butyl ether β-cyclodextrin. In an embodiment, the cyclodextrin is CAPTISOL®. In some embodiments, the cyclodextrin is a β-cyclodextrin disclosed in U.S. Pat. Nos. 5,874,418; 6,046,177; or 7,635,733, which are herein incorporated by reference.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether 3-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In an embodiment, a composition comprising a neuroactive steroid, e.g., allopregnanolone, and cyclodextrin, e.g., β-cyclodextrin, e.g., a sulfo butyl ether β-cyclodextrin, e.g., a β-cyclodextrin, e.g., a sulfo butyl ether β-cyclodextrin, e.g., CAPTISOL®, complex, comprises less than 100 ppm of a phosphate, and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 300 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a color forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 20 ppm of a sulfoalkylating agent; less than 0.5% wt. of an underivatized cyclodextrin; less than 1% wt. of an alkali metal halide salt; and less than 0.25% wt. of a hydrolyzed sulfoalkylating agent.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 50 ppm of a phosphate; less than 10 ppm of a sulfoalkylating agent; less than 0.2% wt. of an underivatized cyclodextrin; less than 0.5% wt. of an alkali metal halide salt; and less than 0.1% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether 3-cyclodextrin, e.g., CAPTISOL®, has an absorption of less than 0.2 A.U. due to the color-forming agent, as determined by U/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 10 ppm of a phosphate; less than 2 ppm of a sulfoalkylating agent; less than 0.1% wt. of an underivatized cyclodextrin; less than 0.2% wt. of an alkali metal halide salt; and less than 0.08% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether 3-cyclodextrin, e.g., CAPTISOL®, has an absorption of less than 0.1 A.U. due to the color-forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 5 ppm of a phosphate; less than 0.1% wt. of an alkali metal halide salt; and less than 0.05% wt. of a hydrolyzed sulfoalkylating agent.

In some embodiments, the neuroactive steroid (e.g., allopregnanolone) and CAPTISOL® complex is formulated as an aqueous composition and is administered within 10 hours, 8 hours, 5 hours, 3 hours, 1 hour, or 0.5 hour after a seizure, e.g., a status epileptic seizure, e.g., a refractory status epileptic seizure has started. In some embodiments, the allopregnanolone and CAPTISOL® complex is formulated as an aqueous composition and is administered within 60 minutes, 45 minutes, 30 minutes, 15 minutes, 10 minutes, or 5 minutes after a seizure, e.g., a status epileptic seizure, e.g., a refractory status epileptic seizure has started. In some embodiments, the neuroactive steroid (e.g., allopregnanolone) and CAPTISOL® complex is formulated as an aqueous composition and is administered after a seizure, e.g., a status epileptic seizure, e.g., a refractory status epileptic seizure has lasted 5 minutes, 10 minutes, 15 minutes, 20 minutes, 30 minutes or 60 minutes.

In some embodiments, the neuroactive steroid (e.g., allopregnanolone) and CAPTISOL® complex is formulated as an aqueous composition and is administered prior to the onset of a seizure, e.g., a status epileptic seizure, e.g., a refractory status epileptic seizure.

In some embodiments, the benzodiazepine is clonazepam, lorazepam, midazolam, or diazepam.

In some embodiments, the benzodiazepine is formulated for oral delivery. In some embodiments, the benzodiazepine is formulated for parenteral delivery (e.g., intranasally, buccally, intravenously or intramuscularly, for example, intravenously or intramuscularly).

In some embodiments, both the neuroactive steroid and the benzodiazepine are formulated for parenteral delivery (e.g., intranasally, buccally, intravenously or intramuscularly, for example, intravenously or intramuscularly).

In some embodiments, the neuroactive steroid such as allopregnanolone and benzodiazepine, when administered in combination, are administered in an amount sufficient to achieve burst suppression (e.g., a predetermined burst suppression pattern, e.g., inter-burst intervals of between 2-30 seconds; as measured by a method of neurophysiological monitoring, e.g., EEG, CFM). In some embodiments, the neuroactive steroid such as allopregnanolone and benzodiazepine, when administered in combination is administered at a dose sufficient to achieve a predetermined burst suppression pattern, e.g., inter-burst intervals of between 2-30 seconds, 5-30 seconds, 10-30 seconds, 15-30 seconds, 1-30 seconds, 0-30 seconds, 2-20 seconds, 2-10 seconds, 5-20 seconds, 10-20 seconds, 15-25 seconds, 5-15 seconds or 5-10 seconds; as measured by a method of neurophysiological monitoring, e.g., EEG, CFM.

In one aspect, the invention features a method of treating a subject (e.g., human subject) having a seizure-related disorder, e.g., status epilepticus (SE), e.g., refractory status epilepticus (RSE) or super-refractory status epilepticus (SRSE), comprising: administering to said subject (e.g., human subject), an effective amount of allopregnanolone, wherein, concurrent with said administering, said subject (e.g., human subject) is under general anesthesia, thereby treating said subject (e.g., human subject).

In one aspect, the invention features a method of treating a subject (e.g., human subject) having a seizure-related disorder, e.g., status epilepticus (SE), e.g., refractory status epilepticus (RSE) or super-refractory status epilepticus (SRSE), comprising administering a first dose, e.g., a load dose, of allopregnanolone, e.g., to a patient under general anesthesia; administering a second dose, e.g., maintenance dose, of allopregnanolone, which is lower than said first dose; and administering a third dose, e.g., a downward taper dose, of allopregnanolone, said allopregnanolone doses being sufficient to treat said subject (e.g., human subject).

In some embodiments, said subject (e.g., human subject) is not under general anesthesia for at least a portion of the second dose. In some embodiments, said subject (e.g., human subject) is not under general anesthesia for at least a portion of the third dose. In some embodiments, said subject (e.g., human subject) is under general anesthesia during the administration of the first dose and during administration of a portion of the second dose, e.g., for at least, or up to, 6, 12, 24, or 47 hours of the second dose.

In some embodiments, the second dose is administered over a period of time that is at least 60, 65, 70, 80, 90, 100, 110, 120 times longer in duration than that of said first dose. In some embodiments, the second dose is administered over a period of time that not more than 80, 90, 100, 110, 120, 130, or 140 times longer in duration than that of said first dose.

In some embodiments, the second dose is administered over a period of time that at least 2, 3, 4, 5, 6 times longer in duration than that of said third dose. In some embodiments, the second dose is administered over a period of time that not more than 5, 6, 7, 8, 9, or 10 times longer in duration than that of said third dose.

In some embodiments, the infusion rate, e.g., amount of allopregnanolone delivered/unit time in the second dose, e.g., as measured in µg/kg/hour, is at least 2, 3, 4, 5, or 6 times lower than that of the first dose.

In some embodiments, one, two or all of said doses are injected, e.g., IV administrations.

In some embodiments, said subject (e.g., human subject) has failed to respond to a first line treatment, e.g., a benzodiazepine (e.g. midazolam), e.g., as evidenced by a failure to induce an EEG pattern of burst suppression, failure to control seizure, continued seizure activity on EEG recording after 24 hours or more on the first line treatment, or failure to wean from the first line treatment without resuming seizure activity as evidenced by EEG recording.

In some embodiments, said subject (e.g., human subject) has failed to respond to a second line treatment, e.g., phenytoin, fos-phenytoin, valproate, phenobarbitol, or levetiracetam, e.g., as evidenced by a failure to induce an EEG pattern of burst suppression, failure to control seizure, continued seizure activity on EEG recording after 24 hours or more on the first line treatment, or failure to wean from the first line treatment without resuming seizure activity as evidenced by EEG recording.

In some embodiments, the method further comprises administering an amount of an aesthetic effective to place said subject (e.g., human subject) under general anesthesia. In some embodiments, said anesthetic is selected from a benzodiazepine (e.g. midazolam), propofol, and pentobarbital.

In some embodiments, the method further comprises a weaning period in which said subject (e.g., human subject) is weaned from said general anesthesia. In some embodiments, said weaning period is initiated during the administration of said second dose. In some embodiments, said weaning period is completed during the administration of said second dose. In some embodiments, said weaning period is initiated within 12, 24, 36, 48, 60 or 72 hours after initiation or completion of the first dose of allopregnanolone. In some embodiments, said weaning period is initiated at 48 hours after initiation or completion of the first dose of allopregnanolone. In some embodiments, said weaning period is 18 to 30 hours, 20 to 28 hours, or 22 to 26 hours in duration. In some embodiments, said weaning period is 24 hours in duration.

In some embodiments, the administration of allopregnanolone, e.g., the first or load dose, is initiated within a preselected period of time, wherein said period begins with: the administration of said anesthetic; or the induction of general anesthesia. In some embodiments, said preselected period is not longer than 48, 24, 12, 6, 5, 4, 3, 2, or 1 hour. In some embodiments, said preselected period is not longer than 120, 60, 30, 15, or 5 minutes.

In some embodiments, said second dose is initiated while the subject (e.g., human subject) is under general anesthesia. In some embodiments, the amount of allopregnanolone delivered per hour in said second dose is the same or lower than the amount delivered per hour in said first dose.

In some embodiments, the administration of the first dose of allopregnanolone is initiated within a preselected period of time, wherein said period begins with: the administration of said anesthetic or the induction of general anesthesia. In some embodiments, said preselected period is at least 6, 12, 24, 48 or 60 hours. In some embodiments, said preselected period is not longer than 24, 48, or 60 hours. In some embodiments, said preselected period is between 2 to 120, 2 to 60, 4 to 120, 4 to 60, 4 to 48, 4 to 36, or 4 to 24 hours. In some embodiments, said preselected period is not longer than 48, 24, 12, 6, 5, 4, 3, 2, or 1 hour. In some embodiments, said preselected period is not longer than 120, 60, 30, 15, or 5 minutes.

In some embodiments, said first dose is begun after failure of the subject (e.g., human subject) to respond to prior treatment. In some embodiments, the failure to respond is evidenced by one or more of, a failure to induce an EEG pattern of burst suppression, failure to control seizure, continued seizure activity on EEG recording after 24 hours or more on the first line treatment, or failure to wean from the first line treatment without resuming seizure activity as evidenced by EEG recording. In some embodiments, said prior treatment comprises administration of a first line treatment, e.g., a benzodiazepine (e.g. midazolam). In some embodiments, said prior treatment comprises administration of a second line treatment, e.g., phenytoin, fos-phenytoin, valproate, phenobarbitol, or levetiracetam.

In some embodiments, said first dose is a load, e.g., bolus, dose. In some embodiments, said first dose results in a plasma concentration of 50 to 500 nM, 100 to 400 nM, or 200 to 300 nM. In some embodiments, said first dose results in a plasma concentration of 500 to 1000 nM, 600 to 900 nM, or 700 to 800 nM. In some embodiments, said first dose results in a plasma concentration of 1000 to 1500 nM, 1100 to 1400 nM, or 1200 to 1300 nM. In some embodiments, said first dose results in a plasma concentration of 1500 to 2000 nM, 1600 to 1900 nM, or 1700 to 1800 nM. In some embodiments, said first dose results in a plasma concentration of 2000 to 2500 nM, 2100 to 2400 nM, or 2200 to 2300 nM. In some embodiments, said first dose results in a plasma concentration of 300 to 800 nM, 400 to 700 nM, or 500 to 600 nM. In some embodiments, said first dose results in a plasma concentration of 800 to 1300 nM, 900 to 1200 nM, or 1000 to 1100 nM. In some embodiments, said first dose results in a plasma concentration of 1300 to 1800 nM, 1400 to 1700 nM, or 1500 to 1600 nM. In some embodiments, said first dose results in a plasma concentration of 1800 to 2300 nM, 1900 to 2200 nM, or 2000 to 2100 nM. In some embodiments, said first dose results in a plasma concentration of 2300 to 2600 nM, 2400 to 2500 nM. In some embodiments, said first dose results in a plasma concentration of 300 to 400 nM, 400 to 500 nM, 600 to 700 nM, 800 to 900 nM, 1100 to 1200 nM, 1300 to 1400 nM, 1400 to 1500 nM, 1600 to 1700 nM, 1800 to 1900 nM, 1900 to 2000 nM, 2100 to 2200 nM, 2300 to 2400 nM. In some embodiments, said first dose results in a plasma concentration of 500 to 2500 nM, 500 to 1500 nM, 500 to 1000 nM, 500 to 800, or 500 to 600, nM. In some embodiments, said first dose results in a plasma concentration of 50 to 250 nM, 100 to 200 nM, or 140 to 160 nM. In some embodiments, said first dose results in a plasma concentration of 150+/−30 nM, 150+/−20 nM, 150+/−10 nM, or 150 nM.

In some embodiments, the plasma concentration of said first dose is measured at a preselected time, e.g., at 10, 15, 20, 30, 45, 60 minutes, 2, 3, 4, 5, 6, 8, 10, 12, 24 hours, 2, 3, 4 days after the initiation of said first dose.

In some embodiments, said first dose is administered over a period of time that is not longer than 6, 5, 4, 3, 2, or 1 hour. In some embodiments, said first dose is administered over a period of time that is at least 10, 20, 30, 40, 50, 60, 70, 80, or 90 minutes in duration. In some embodiments, said first dose is administered over a period of time that is 30 to 120 minutes, 45 to 100 minutes, or 50 to 70 minutes, in duration. In some embodiments, said first dose is administered over a period of time that is 60+/−15 minutes, 60+/−10 minutes, 60+/−5 minutes, or 60 minutes, in duration.

In some embodiments, said first dose is administered at a dosage rate of 200-3500 μg/kg/hour. In some embodiments, said first dose is administered at a dosage rate of 200-350 μg/kg/hour, 250-300 μg/kg/hour, 280-290 μg/kg/hour, 286 μg/kg/hour, 287 μg/kg/hour, or 288 μg/kg/hour, e.g., for one hour.

In some embodiments, said second dose is a maintenance dose. In some embodiments, the administration said second dose is initiated within a preselected time period, wherein said time period begins with the administration of said anesthetic. In some embodiments, the administration said second dose is initiated within a preselected time period, wherein said time period begins with the induction of general anesthesia. In some embodiments, the administration said second dose is initiated within a preselected time period, wherein said time period begins with the beginning of the first dose. In some embodiments, the administration said second dose is initiated within a preselected time period, wherein said time period begins with the end of the first dose. In some embodiments, the administration said second dose is initiated within a preselected time period, wherein said time period begins with the achievement of a predetermined level of allopregnanolone, e.g., in the plasma. In some embodiments, said time period begins with the end of the first dose. In some embodiments, said preselected time period begins with beginning or ending of the administration of the first dose and is not longer than 240, 180, 120, 60, 30, 15, or 5 minutes. In some embodiments, said preselected time period begins with beginning or ending of the administration of the first dose and is not longer than 90, 80, 70, or 60 minutes. In some embodiments, the administration of the second dose begins no longer than 90, 80, 70, 60, or 30 minutes after the beginning or end of the administration of the first dose. In some embodiments, the administration of the second dose begins 50 to 70, 55 to 65, or 60 minutes after the beginning or end of the administration of the first dose. In some embodiments, the administration of the second dose begins no more than 60, 50, 40, 30, 20, 10, 5, 4, 3, 2, 1 minute after the end of administration of the first dose. In some embodiments, the administration of the second dose begins at the end of administration of the first dose.

In some embodiments, the administration of the first dose and the initiation of second dose are performed with the same delivery device, e.g., with the same cannula or reservoir.

In some embodiments, said second dose is administered for a period of time that is between 48 and 192 hours, 60 and 144 hours, 60 and 120 hours, 80 and 110 hours, and 90 and 100 hours. In some embodiments, said second dose is administered for 95+/−5 hours. In some embodiments, said second dose is administered for 95 hours.

In some embodiments, said second dose results in a plasma concentration of 50 to 500 nM, 100 to 400 nM, or 200 to 300 nM. In some embodiments, said second dose results in a plasma concentration of 500 to 1000 nM, 600 to 900 nM, or 700 to 800 nM. In some embodiments, said second dose results in a plasma concentration of 1000 to 1500 nM, 1100 to 1400 nM, or 1200 to 1300 nM. In some embodiments, said second dose results in a plasma concentration of 1500 to 2000 nM, 1600 to 1900 nM, or 1700 to 1800 nM. In some embodiments, said second dose results in a plasma concentration of 2000 to 2500 nM, 2100 to 2400 nM, or 2200 to 2300 nM. In some embodiments, said second dose results in a plasma concentration of 300 to 800 nM, 400 to 700 nM, or 500 to 600 nM. In some embodiments, said second dose results in a plasma concentration of 800 to 1300 nM, 900 to 1200 nM, or 1000 to 1100 nM. In some embodiments, said first dose results in a plasma concentration of 1300 to 1800 nM, 1400 to 1700 nM, or 1500 to 1600 nM. In some embodiments, said second dose results in a plasma concentration of 1800 to 2300 nM, 1900 to 2200 nM, or 2000 to 2100 nM. In some embodiments, said second dose results in a plasma concentration of 2300 to 2600 nM, 2400 to 2500 nM. In some embodiments, said second dose results in a plasma concentration of 300 to 400 nM, 400 to 500 nM, 600 to 700 nM, 800 to 900 nM, 1100 to 1200 nM, 1300 to 1400 nM, 1400 to 1500 nM, 1600 to 1700 nM, 1800 to 1900 nM, 1900 to 2000 nM, 2100 to 2200 nM, 2300 to 2400 nM. In some embodiments, said second dose results in a plasma concentration of 500 to 2500 nM, 500 to 1500 nM, 500 to 1000 nM, 500 to 800 nM, or 500 to 600 nM. In some embodiments, said second dose results in a plasma concentration of 50 to 250 nM, 100 to 200 nM, or 140 to 160 nM. In some embodiments, said second dose results in a plasma concentration of 150+/−30 nM, 150+/−20 nM, 150+/−10 nM, or 150 nM In some embodiments, the plasma concentration of said second dose is measured at a preselected time, e.g., at 10, 15, 20, 30, 45, 60 minutes, 2, 3, 4, 5, 6, 8, 10, 12, 24 hours, 2, 3, 4 days after the initiation of said second dose.

In some embodiments, said second dose results in a plasma concentration of 150 nM, e.g., as measured at a preselected time, e.g., at 10, 15, 20, 30, 45, 60 minutes, 2, 3, 4, 5, 6, 8, 10, 12, 24 hours, 2, 3, 4 days after the initiation of said second dose.

In some embodiments, said second dose is administered at the same infusion rate, e.g. amount of allopregnanolone/unit time, over the entire second dose. In some embodiments, the infusion rate, e.g. amount of allopregnanolone delivered/unit time varies during the second dose. In some embodiments, said second dose is administered at an infusion rate, e.g. amount of allopregnanolone/unit time of 25-1500 µg/kg/hour. In some embodiments, said second dose is administered at an infusion rate, e.g. amount of allopregnanolone/unit time of 25-150 µg/kg/hour, 50-100 µg/kg/hour, 75-100 µg/kg/hour, 85 µg/kg/hour, 86 µg/kg/hour, or 87 µg/kg/hour.

In some embodiments, said downward taper dose comprises administering a continuously decreasing amount allopregnanolone. In some embodiments, said downward taper dose comprises administering a continuously decreasing amount of allopregnanolone/unit time. In some embodiments, said downward taper dose comprises administering a plurality of step doses, wherein each subsequent step dose is lower than the step dose that precedes it. In some embodiments, said downward taper dose comprises administering a plurality of step doses, wherein each subsequent step dose delivers a lower amount of allopregnanolone/unit time than the step dose that precedes it.

In some embodiments, the method comprises administering a first, second, and third step dose. In some embodiments, said first step dose is 60 to 90% of the second/maintenance dose; said second step dose is 40 to 70% of the second/maintenance dose; and said third step dose is 10 to 40% of the second/maintenance dose. In some embodiments, the amount of allopregnanolone delivered/unit time in said first step dose is 60 to 90% of the amount of allopregnanolone delivered/unit time in said second/maintenance dose; the amount of allopregnanolone delivered/unit time in said second step dose is 40 to 70% of the amount of allopregnanolone delivered/unit time in said second/maintenance dose; and the amount of allopregnanolone delivered/unit time in said third step dose is 10 to 40% of the infusion rate, e.g. amount of allopregnanolone delivered/unit time in said second/maintenance dose. In some embodiments, said first step dose is 70 to 80% of the second/maintenance dose; said second step dose is 40 to 60% of the second/maintenance dose; and said third step dose is 20 to 30% of the second/maintenance dose. In some embodiments, the amount of allopregnanolone delivered/unit time in said first step dose is 70 to 80% of the amount of allopregnanolone delivered/unit time in said second/maintenance dose; the amount of allopregnanolone delivered/unit time in said second step dose is 40 to 60% of the amount of allopregnanolone delivered/unit time in said second/maintenance dose; and the amount of allopregnanolone delivered/unit time in said third step dose is 20 to 30% of the amount of allopregnanolone delivered/unit time in said second/maintenance dose. In some embodiments, said first step dose is 75% of the second/maintenance dose; said second step dose is 50% of the second/maintenance dose; and said third step dose is 25% of the second/maintenance dose. In some embodiments, the amount of allopregnanolone delivered/unit time in said first step dose is 75% of the amount of allopregnanolone delivered/unit time in said second/maintenance dose. In some embodiments, the amount of allopregnanolone delivered/unit time in said second step dose is 50% of the amount of allopregnanolone delivered/unit time in said second/maintenance dose. In some embodiments, the amount of allopregnanolone delivered/unit time in said third step dose is 25% of the amount of allopregnanolone delivered/unit time in said second/maintenance dose.

In some embodiments, after the completion of said third step dose, no allopregnanolone is administered to the subject (e.g., human subject) for at least 10, 20, 30, 40, 50, or 60 days, or until the patient has a subsequent episode of SRSE.

In some embodiments, said first step dose is administered at an amount of allopregnanolone/unit time of 25-1000 μg/kg/hour. In some embodiments, said first step dose is administered at an amount of allopregnanolone/unit time of 25-100 μg/kg/hour, 50-75 μg/kg/hour, 60-70 μg/kg/hour, 63 μg/kg/hour, 64 μg/kg/hour, or 65 μg/kg/hour. In some embodiments, said second step dose is administered at an amount of allopregnanolone/unit time of 10-700 μg/kg/hour. In some embodiments, said second step dose is administered at an amount of allopregnanolone/unit time of 10-70 μg/kg/hour, 25-55 μg/kg/hour, 40-50 μg/kg/hour, 42 μg/kg/hour, 43 μg/kg/hour, or 44 μg/kg/hour. In some embodiments, said third step dose is administered at an amount of allopregnanolone/unit time of 5-500 μg/kg/hour. In some embodiments, said third step dose is administered at an amount of allopregnanolone/unit time of 5-50 μg/kg/hour, 10-35 μg/kg/hour, 15-25 μg/kg/hour, 20 μg/kg/hour, 21 μg/kg/hour, or 22 μg/kg/hour.

In some embodiments, the third/taper dose begins no longer than 90, 80, 70, 60, or 30 minutes after the administration or end of the second dose. In some embodiments, the third/taper dose begins at the end of administration of the second dose.

In some embodiments, the administration of the second dose and the initiation of third/taper dose are performed with the same delivery device, e.g., the same cannula.

In some embodiments, the time between the end of the administration of said first step dose and the initiation of administration of said second step dose is less than 120, 60, 30, 15 or 5 minutes.

In some embodiments, the time between the end of the administration of said second step dose and the initiation of administration of said third step dose is less than 120, 60, 30, 15 or 5 minutes.

In some embodiments, said third dose is administered for a period of time that is between 10 and 100 hours, 12 and 96 hours, 12 and 48 hours, 16 and 32 hours, or 20 and 30 hours.

In some embodiments, said third dose is administered over 24 hours.

In some embodiments, the allopregnanolone is provided in a composition comprising a cyclodextrin, e.g., β-cyclodextrin, e.g., sulfo butyl ether β-cyclodextrin, e.g., CAPTISOL. In some embodiments, the allopregnanolone is provided at a concentration of 0.1 to 10 mg/mL allopregnanolone. In some embodiments, the allopregnanolone is provided at a concentration of 0.1, 0.5, 1, 1.25, 2.5, 3.75, 5, 6.25, 7.5, 8, 9, or 10 mg/mL allopregnanolone. In some embodiments, the allopregnanolone is provided at a concentration of 1.25 mg/mL allopregnanolone. In some embodiments, the allopregnanolone is provided at a concentration of 2.5 mg/mL allopregnanolone. In some embodiments, the allopregnanolone is provided at a concentration of 3.75 mg/mL allopregnanolone. In some embodiments, the allopregnanolone is provided at a concentration of 5 mg/mL allopregnanolone.

In some embodiments, the cyclodextrin is present in the composition at 1-30%, 2-18%, 10-15% by weight of cyclodextrin per volume of composition. In some embodiments, the cyclodextrin is present in the composition at 1, 2.5, 5, 10, 12, 13, 15, 30% by weight of cyclodextrin per volume of composition. In some embodiments, the cyclodextrin is present in the composition at 12% by weight of cyclodextrin per volume of composition.

In some embodiments, the cyclodextrin is present in the composition at 1-30%, 2-18%, 10-15% by weight of cyclodextrin per volume of composition and the allopregnanolone is provided at a concentration of 0.1, 0.5, 1, 1.25, 2.5, 3.75, 5, 6.25, 7.5, 8, 9, or 10 mg/mL allopregnanolone. In some embodiments, the cyclodextrin is present in the composition at 1, 2.5, 5, 10, 12, 13, 15, 30% by weight of cyclodextrin per volume of composition and the allopregnanolone is provided at a concentration of 0.1, 0.5, 1, 1.25, 2.5, 3.75, 5, 6.25, 7.5, 8, 9, or 10 mg/mL allopregnanolone.

In some embodiments, the cyclodextrin is present in the composition at 12% by weight of cyclodextrin per volume of composition and the allopregnanolone is provided at a concentration of 5 mg/mL allopregnanolone. In some embodiments, the cyclodextrin is present in the composition at 12% by weight of cyclodextrin per volume of composition and the allopregnanolone is provided at a concentration of 3.75 mg/mL allopregnanolone. In some embodiments, the cyclodextrin is present in the composition at 12% by weight of cyclodextrin per volume of composition and the allopregnanolone is provided at a concentration of 2.5 mg/mL allopregnanolone. In some embodiments, the cyclodextrin is present in the composition at 12% by weight of cyclodextrin per volume of composition and the allopregnanolone is provided at a concentration of 1.25 mg/mL allopregnanolone.

In some embodiments, the method further comprises, evaluating the subject (e.g., human subject), wherein the evaluating comprises performing c-ECG. In some embodiments, the method comprises, evaluating the subject (e.g., human subject), wherein the evaluating comprises performing EEG. In some embodiments, the method further comprises evaluating the subject (e.g., human subject) for serum chemistry (e.g., one or more of albumin, AST, ALT, bicarbonate, bilirubin, BUN, calcium, chloride, creatine kinase, lipase, creatinine, magnesium, potassium, sodium, total protein, or glucose). In some embodiments, the method further comprises, evaluating the subject (e.g., human subject) for CBC (e.g., one or more of RBC, hemoglobin, hematocrit, MCV, MCH, MCHC, platelet count, WBC with differential including neutrophils, eosinophils, basophils, lymphocytes, or monocytes. In some embodiments, the method further comprises evaluating the subject (e.g., human subject) for serum allopregnanolone, progesterone, and 5α-dihydrotestosterone. In some embodiments, the method comprises comparing an observed value with a reference value.

In some embodiments, said subject (e.g., human subject) is evaluated for a parameter described herein during said weaning period.

In one aspect, the invention features a method of treating a subject (e.g., human subject) having, SE, RSE, or SRSE comprising: administering a first/load, e.g., bolus, dose concurrent with general anesthesia, wherein administration of said first dose: begins 2-120 hours after induction of general anesthesia; lasts for 30-90 minutes; and results in a plasma level of allopregnanolone of 100-2000 nM allopregnanolone; administering a second/maintenance dose, wherein, the administration of said second dose begins not longer than 1-60 minutes after the end of the second dose; lasts for 1-6 days; and results in a plasma level of allopregnanolone of 100-2000 nM allopregnanolone; administering a third downward taper dose, wherein, the administration of said third downward taper dose begins not longer than 1-60 minutes after the end of the third dose; lasts for 10-100 hours; and results in a plasma level of allopregnanolone of 0-1500 nM allopregnanolone; wherein, collectively, the administrations are provided in sufficient amount to treat said subject (e.g., human subject).

In some embodiments, the method comprises administering a first/load, e.g., bolus, dose concurrent with general anesthesia, wherein administration of said first dose: begins 2-120 hours after induction of general anesthesia; lasts for 60+/−15 minutes; administering a second/maintenance dose, wherein, the administration of said second dose begins not longer than 30 minutes after the end of the second dose; lasts for 70 to 110 hours; administering a third downward taper dose, wherein, the administration of said third downward taper dose begins not longer than 1-60 minutes after the end of the third dose; lasts for 10-30 hours.

In some embodiments, administering a first/load, e.g., bolus, dose concurrent with general anesthesia, wherein administration of said first dose: begins 2-120 hours after induction of general anesthesia; lasts for 60+/−15 minutes; administering a second/maintenance dose, wherein, the administration of said second dose begins not longer than 30 minutes after the end of the second dose; lasts for 70 to 110 hours; and administering a third downward taper dose, wherein, the administration of said third downward taper dose begins not longer than 1-60 minutes after the end of the third dose; lasts for 24+/−2 hours and said third downward taper dose comprises a first, second, and third step dose.

In some embodiments, administering a first/load, e.g., bolus, dose concurrent with general anesthesia, wherein administration of said first dose lasts for 60+/−15 minutes; administering a second/maintenance dose, wherein, the administration of said second dose begins not longer than 30 minutes after the end of the second dose; lasts for 85 to 105 hours; administering a third downward taper dose, wherein, the administration of said third downward taper dose begins not longer than 1-60 minutes after the end of the third dose; lasts for 10-30 hours and: the amount of allopregnanolone delivered/unit time in said first step dose is 70 to 80% of the amount of allopregnanolone delivered/unit time in said second/maintenance dose; the amount of allopregnanolone delivered/unit time in said second step dose is 40 to 60% of the amount of allopregnanolone delivered/unit time in said second/maintenance dose; and the amount of allopregnanolone delivered/unit time in said third step dose is 20 to 30% of the amount of allopregnanolone delivered/unit time in said second/maintenance dose.

In some embodiments, administering a first/load, e.g., bolus, dose concurrent with general anesthesia, wherein administration of said first dose lasts for 60+/−5 minutes; administering a second/maintenance dose, wherein, the administration of said second dose begins not longer than 30 minutes after the end of the second dose; lasts for 96+/−4 hours; administering a third downward taper dose, wherein, the administration of said third downward taper dose begins not longer than 1-60 minutes after the end of the third dose; lasts for 24+/−2 hours and: the amount of allopregnanolone delivered/unit time in said first step dose is 75% of the amount of allopregnanolone delivered/unit time in said second/maintenance dose; the amount of allopregnanolone delivered/unit time in said second step dose is 50% of the amount of allopregnanolone delivered/unit time in said second/maintenance dose; and the amount of allopregnanolone delivered/unit time in said third step dose is 25% of the amount of allopregnanolone delivered/unit time in said second/maintenance dose.

In some embodiments, the method further comprises administering an amount of a composition selected from benzodiazepines (e.g., midazolam), propofol, barbiturates, and ketamine sufficient to place said subject (e.g., human subject) under general anesthesia;

In one aspect, the invention features a kit comprising one or more of: a preparation of allopregnanolone, e.g., a plurality of preparations of allopregnanolone at a concentrations suitable for use at the first, second, and third doses; and instructions for use for treating a subject (e.g., human subject) having a seizure-related disorder, e.g., status epilepticus (SE), e.g., super-refractory status epilepticus (SRSE).

In some embodiments, the kit further comprises a suitable diluent (e.g., water, saline, cyclodextrin, e.g., β-cyclodextrin, e.g., sulfo butyl ether β-cyclodextrin, e.g., CAPTISOL).

In some embodiments, the allopregnanolone is provided at a concentration of 0.1-10 mg/mL allopregnanolone. In some embodiments, the allopregnanolone is provided at a concentration of 0.5-7.5 mg/mL allopregnanolone. In some embodiments, the allopregnanolone is provided at a concentration of 1-6 mg/mL allopregnanolone. In some embodiments, the allopregnanolone is provided at a concentration of 5 mg/mL allopregnanolone. In some embodiments, the allopregnanolone is provided at a concentration of 3.75 mg/mL allopregnanolone. In some embodiments, the allopregnanolone is provided at a concentration of 2.5 allopregnanolone. In some embodiments, the allopregnanolone is provided at a concentration of 1.25 mg/mL allopregnanolone.

In one aspect, the invention features a method of making a series of dosages, the method comprising combining a diluent and allopregnanolone in proportions to from dosage forms suitable for use as the first, second and one or more step doses for said third dose.

In one aspect, the invention features a method of adjusting the amount of diluents and or allopregnanolone flowing into or out of a delivery device, e.g., a catheter, reservoir, the method comprising altering, e.g., decreasing, the flow rate of allopregnanolone flowing into the delivery device, so as to release in succession, two or more of a first dosage, a second dosage and one or more step doses of the third dose.

In one aspect, the invention features a method of treating a subject having seizure, epilepsy or status epilepticus by administering in combination to the subject a neuroactive steroid and a benzodiazepine or anesthetic/sedative. In some embodiments, the method further comprises administering at least one of the neuroactive steroid and benzodiazepine or anesthetic/sedative parenterally (e.g., intranasally, buccally, intravenously or intramuscularly, for example, intravenously or intramuscularly). In some embodiments, both the neuroactive steroid and benzodiazepine or anesthetic/sedative are administered parenterally.

In some embodiments, the neuroactive steroid and benzodiazepine or anesthetic/sedative co-administered (e.g., administered simultaneously, administered concurrently). In some embodiments, the neuroactive steroid and benzodiazepine or anesthetic/sedative are administered sequentially. In some embodiments, neuroactive steroid and benzodiazepine or anesthetic/sedative are administered in a single dosage form.

When the agents described herein (e.g., the neuroactive steroid and a benzodiazepine or anesthetic/sedative) are administered in combination, both of the agents should be present at dosage levels of between about 1 to 100%, and more preferably between about 5 to 95% of the dosage normally administered in the absence of the combination regimen. The agents may be administered separately, as part of a multiple dose regimen. Alternatively, the agents may be part of a single dosage form, mixed together with the compounds of this invention in a single composition.

In some embodiments, the neuroactive steroid is a progestin derivative, e.g., allopregnanolone. In an embodiment, the neuroactive steroid is allopregnanolone.

In some embodiments, the neuroactive steroid, e.g., allopregnanolone, is formulated for parenteral administration (e.g., intranasally, buccally, intravenously or intramuscularly, for example, intravenously or intramuscularly).

In some embodiments, the neuroactive steroid, e.g., allopregnanolone, is administered in a composition comprising a cyclodextrin, e.g., a β-cyclodextrin, e.g., a sulfo butyl ether β-cyclodextrin, e.g., CAPTISOL®, complex.

In some embodiments, the cyclodextrin is a β-cyclodextrin. In an embodiment, the cyclodextrin is a sulfo butyl ether β-cyclodextrin. In an embodiment, the cyclodextrin is CAPTISOL®. In some embodiments, the cyclodextrin is a β-cyclodextrin disclosed in U.S. Pat. Nos. 5,874,418; 6,046,177; or 7,635,733, which are herein incorporated by reference.

In some embodiments, the neuroactive steroid is a progestin derivative, e.g., allopregnanolone, and the cyclodextrin is a β-cyclodextrin. In some embodiments, the neuroactive steroid is a progestin derivative, e.g., allopregnanolone, and the cyclodextrin is a sulfo butyl ether β-cyclodextrin. In an embodiment, the neuroactive steroid is allopregnanolone and the cyclodextrin is CAPTISOL®.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL; 0.25-30 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 0.5-7 mg/mL; 1-15 mg/mL, 1-10 mg/mL; 1-7 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 3-7 mg/mL; 4-6 mg/mL; 7-12 mg/mL; 7-10 mg/mL; 8-9 mg/mL; 3-5 mg/mL; or 3-4 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg/mL, or 30 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 2.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 3.5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 6 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of between 0.1-50 μM; 0.1-40 μM; 0.1-30 μM; 0.1-20 μM; 0.1-15 μM; 0.5-50 μM; 0.5-40 μM; 0.5-30 μM; 0.5-20 μM; 0.5-15 μM; 1-50 μM; 1-40 μM; 1-30 μM; 1-20 μM; 1-15 μM; 2-50 μM; 2-40 μM; 2-30 μM; 2-20 μM; 2-15 μM; 0.5-15 μM; 1-15 μM; 2-15 μM; 3-15 μM; 1-20 μM. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.1 μM; 0.5-1 μM; 2 μM; 4 μM; 5 μM; 7 μM; 10 μM; 15 μM; 20 μM; 25 μM; 40 μM; 50 μM. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1 μM. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 2 μM. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 μM.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 30-300 mg/mL; 30-400 mg/mL; 45-75 mg/mL; 50-70 mg/mL; 55-65 mg/mL; or 50-60 mg/mL. In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/mL.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-15%, 2.5-10%, 5-40%, 5-30%, 5-20%, 5-15%, 5-10%, 6-40%, 6-30%, 6-20%, 6-10%, 6-20%, 6-30%, 10-40%, 10-30%, 10-20%, 20-40%, 20-30%, 25-40%, 25-30%, 3-10%, 3-15%, 4.5-7.5%, 4-13%, 5-7%, 5-13%, 5.5-6.5%, 7-13% by weight of the cyclodextrin, e.g., CAPTISOL® per weight of solution.

In some embodiments, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 12%, 15%, 20%, 25%, 30%, 35% or 40% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 6% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 15% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising 30% by weight of the cyclodextrin, e.g., CAPTISOL® per weight of solution.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 6% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 6% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 6% by weight of the cyclodextrin, e.g., CAPTISOL® per weight of solution.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.25 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 2.5 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 3.75 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 5 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 12% by weight of the cyclodextrin, e.g., CAPTISOL® per weight of solution.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 15% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 15% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 15% by weight of the cyclodextrin, e.g., CAPTISOL® per weight of solution.

In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 1.5 mg/mL, and the cyclodextrin, e.g., a β-cyclodextrin, e.g., a sulfo butyl ether β-cyclodextrin, e.g., CAPTISOL®, at a concentration of 30% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 10 mg/mL, and the cyclodextrin, e.g., a β-cyclodextrin, e.g., a sulfo butyl ether β-cyclodextrin, e.g., CAPTISOL®, at a concentration of 30% by weight of the cyclodextrin, e.g., CAPTISOL® per weight of solution. In an embodiment, the neuroactive steroid, e.g., allopregnanolone, and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., allopregnanolone, at a concentration of 15 mg/mL, and the cyclodextrin, e.g., a β-cyclodextrin, e.g., a sulfo butyl ether β-cyclodextrin, e.g., CAPTISOL®, at a concentration of 30% by weight of the cyclodextrin, e.g., CAPTISOL® per weight of solution.

In some embodiments, the allopregnanolone and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the allopregnanolone and CAPTISOL® complex is formulated as an aqueous composition with a pH about 3, 3.5, 4, 4.5, 5, 5.5, 6, 6.5, 7, 7.5, 8, 8.5, or 9. In an embodiment, the allopregnanolone and CAPTISOL® complex is formulated as an aqueous composition with a pH about 6.

In some embodiments, the allopregnanolone and CAPTISOL® complex is formulated as an aqueous composition and is administered intravenously. In some embodiments, the allopregnanolone and CAPTISOL® complex is formulated as an aqueous composition and is administered intramuscularly.

In some embodiments, the allopregnanolone and CAPTISOL® complex is formulated as an aqueous composition and is administered for 1, 2, 3, 4, 5, 6, 7, 8, 9, or 10 consecutive days. In some embodiments, the allopregnanolone and CAPTISOL® complex is formulated as an aqueous composition and is administered between 1-10, 1-5, 5-10, 1-6, 2-6, 3-6, 4-5, or 1-9 consecutive days. In an embodiment, the allopregnanolone and CAPTISOL® complex is formulated as an aqueous composition and is administered for 5 consecutive days. In some embodiments, the duration of administration is 1, 2, 3, 4, 5, 6, 7, 8, 9, or 10 days. In some embodiments, the duration of administration is 3-7, 4-6, 4-5, or 5-6 days. In some embodiments, the duration of administration is 5 days.

In some embodiments, the allopregnanolone and CAPTISOL® complex is formulated as an aqueous composition and is administered at the same dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days. In an embodiment, the allopregnanolone and CAPTISOL® complex is formulated as an aqueous composition and is administered at a load, e.g., bolus, dose of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg/mL, or 30 mg/mL neuroactive steroid, e.g., allopregnanolone, for 1 day and then administered at a maintenance, e.g., infusion, dose for 1, 2, 3, 4, 5, or 6 consecutive days of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg/mL, or 30 mg/mL neuroactive steroid, e.g., allopregnanolone. In some embodiments, a maintenance, e.g., infusion, dose described herein, is lower than a load, e.g., bolus, dose described herein. In some embodiments, a maintenance, e.g., infusion, dose described herein, is the same as a load, e.g., bolus, dose described herein. In some embodiments, the maintenance, e.g., infusion, dose is less than 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg/mL, or 30 mg/mL.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a taper dose for 1, 2, 3, 4, 5, 6, 7, 8, 9, or 10 consecutive days. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first step dose for 1, 2, 3, 4, 5, 6, 7, 8, 9, or 10 hours.

In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first step dose for 1, 2, 3, 4, 5, 6, 7, 8, 9, or 10 hours and then administered at a second step dose for 1, 2, 3, 4, 5, 6, 7, 8, 9, or 10 hours. In some embodiments, the allopregnanolone and CAPTISOL® complex is formulated as an aqueous composition and is administered at a load, e.g., bolus, dose for 1, 2, 3, 4, 5, 6, 7, 8, 9, or 10 consecutive days and then administered at a maintenance, e.g., infusion, dose for 1, 2, 3, 4, 5, 6, 7, 8, 9, or 10 consecutive days and then administered at a first step dose for 1, 2, 3, 4, 5, 6, 7, 8, 9, or 10 hours and then administered at a second step dose for 1, 2, 3, 4, 5, 6, 7, 8, 9, or 10 hours and then administered at a third step dose for 1, 2, 3, 4, 5, 6, 7, 8, 9, or 10 hours.

In some embodiments the first, second, or third step dose is less than the maintenance, e.g., infusion, dose. In some embodiments, the second taper or third step dose is less than the first step dose. In some embodiments, the third step dose is less than the second step dose. In some embodiments, the first step dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the first step dose is between 95-50%, 75-50%, 85-50%, 90-50%, 80-50%, or 75-100% of the maintenance, e.g., infusion, dose. In an embodiment, the first step dose is 75% of the maintenance, e.g., infusion, dose.

In some embodiments, the second step dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the second step dose is between 95-30%, 75-30%, 85-30%, 60-30%, 70-30%, 50-30%, or 50-40% of the maintenance, e.g., infusion, dose. In an embodiment, the second step dose is 50% of the maintenance, e.g., infusion, dose.

In some embodiments, the third step dose is 95%, 90%, 85%, 80%, 75%, 70%, 65%, 60%, 55%, 50%, 45%, 40%, 35%, 30%, 25%, 20%, 15%, 10%, or 5% of the maintenance, e.g., infusion, dose. In some embodiments, the third step dose is between 50-5%, 40-5%, 30-5%, 25-5%, 25-10%, 25-20%, or 25-40% of the maintenance, e.g., infusion, dose. In an embodiment, the second step dose is 50% of the maintenance, e.g., infusion, dose. In an embodiment, the third step dose is 25% of the maintenance, e.g., infusion, dose.

In an embodiment, a composition comprising a neuroactive steroid, e.g., allopregnanolone, and cyclodextrin, e.g., a β-cyclodextrin, e.g., a sulfo butyl ether β-cyclodextrin, e.g., CAPTISOL®, complex, comprises less than 100 ppm of a phosphate, and the cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 300 mg of the cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., CAPTISOL®, has an absorption of less than 0.2 A.U. due to a color forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., CAPTISOL®, further comprises: less than 20 ppm of a sulfoalkylating agent; less than 0.5% wt. of an underivatized cyclodextrin; less than 1% wt. of an alkali metal halide salt; and less than 0.25% wt. of a hydrolyzed sulfoalkylating agent.

In some embodiments, the cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 500 mg of the cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., CAPTISOL®, further comprises: less than 50 ppm of a phosphate; less than 10 ppm of a sulfoalkylating agent; less than 0.2% wt. of an underivatized cyclodextrin; less than 0.5% wt. of an alkali metal halide salt; and less than 0.1% wt. of a hydrolyzed sulfoalkylating agent; and wherein the cyclodextrin, e.g., a β-cyclodextrin, e.g., a sulfo butyl ether β-cyclodextrin, e.g., CAPTISOL®, has an absorption of less than 0.2 A.U. due to the color-forming agent, as determined by U/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., CAPTISOL®, further comprises: less than 10 ppm of a phosphate; less than 2 ppm of a sulfoalkylating agent; less than 0.1% wt. of an underivatized cyclodextrin; less than 0.2% wt. of an alkali metal halide salt; and less than 0.08% wt. of a hydrolyzed sulfoalkylating agent; and wherein the cyclodextrin, e.g., a β-cyclodextrin, e.g., a sulfo butyl ether β-cyclodextrin, e.g., CAPTISOL®, has an absorption of less than 0.1 A.U. due to the color-forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., CAPTISOL®, further comprises: less than 5 ppm of a phosphate;

less than 0.1% wt. of an alkali metal halide salt; and less than 0.05% wt. of a hydrolyzed sulfoalkylating agent.

In some embodiments, the neuroactive steroid (e.g., allopregnanolone) and CAPTISOL® complex is formulated as an aqueous composition and is administered within 48 hours, 24 hours, 10 hours, 8 hours, 5 hours, 3 hours, 1 hour, or 0.5 hour after a seizure, e.g., a status epileptic seizure, e.g., a refractory status epileptic seizure has started. In some embodiments, the allopregnanolone and CAPTISOL® complex is formulated as an aqueous composition and is administered within 60 minutes, 45 minutes, 30 minutes, 15 minutes, 10 minutes, or 5 minutes after a seizure, e.g., a status epileptic seizure, e.g., a refractory status epileptic seizure has started. In some embodiments, the neuroactive steroid (e.g., allopregnanolone) and CAPTISOL® complex is formulated as an aqueous composition and is administered after a seizure, e.g., a status epileptic seizure, e.g., a refractory status epileptic seizure has lasted 5 minutes, 10 minutes, 15 minutes, 20 minutes, 30 minutes or 60 minutes.

In some embodiments, the neuroactive steroid (e.g., allopregnanolone) and CAPTISOL® complex is formulated as an aqueous composition and is administered prior to the onset of a seizure, e.g., a status epileptic seizure, e.g., a refractory status epileptic seizure.

In some embodiments, the benzodiazepine is clonazepam, lorazepam, midazolam, or diazepam.

In some embodiments, the benzodiazepine is formulated for oral delivery. In some embodiments, the benzodiazepine is formulated for parenteral delivery (e.g., intranasally, buccally, intravenously or intramuscularly, for example, intravenously or intramuscularly).

In some embodiments, the anesthetic/sedative is propofol or a barbiturate, e.g., pentobarbital.

In some embodiments, both the neuroactive steroid and the benzodiazepine or anesthetic/sedative are formulated for parenteral delivery (e.g., intranasally, buccally, intravenously or intramuscularly, for example, intravenously or intramuscularly).

In some embodiments, the neuroactive steroid such as allopregnanolone and benzodiazepine or anesthetic/sedative, when administered in combination, are administered in an amount sufficient to achieve burst suppression (e.g., a predetermined burst suppression pattern, e.g., inter-burst intervals of between 2-30 seconds; as measured by a method of neurophysiological monitoring, e.g., EEG, CFM). In some embodiments, the neuroactive steroid such as allopregnanolone and benzodiazepine or anesthetic/sedative, when administered in combination, is administered at a dose sufficient to achieve a predetermined burst suppression pattern, e.g., inter-burst intervals of between 2-30 seconds, 5-30 seconds, 10-30 seconds, 15-30 seconds, 1-30 seconds, 0-30 seconds, 2-20 seconds, 2-10 seconds, 5-20 seconds, 10-20 seconds, 15-25 seconds, 5-15 seconds or 5-10 seconds; as measured by a method of neurophysiological monitoring, e.g., EEG, CFM.

DETAILED DESCRIPTION OF THE INVENTION

Figure 1:
FIG. 1. Physical appearance of ALLO formulations with Captisol.

As used herein, "administered in combination" or a combined administration of two agents (e.g., a neuroactive steroid and a benzodiazepine or anesthetic/sedative) means that two or more agents are administered to a subject at the same time or within an interval such that there is overlap of an effect of each agent on the patient. Preferably they are administered within 15, 10, 5, or 1 minute of one another. Preferably the administrations of the agents are spaced sufficiently close together such that a combinatorial effect is achieved. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject. In an embodiment, the agents (e.g., a neuroactive steroid and a benzodiazepine or anesthetic/sedative) are administered essentially simultaneously, for example two unit dosages administered at the same time, or a combined unit dosage of the two agents. In another embodiment, the agents are delivered in separate unit dosages. The agents can be administered in any order, or as one or more preparations that includes two or more agents. In an embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 20, 50, 70, or 100% greater than additive.

As used herein, "concurrent" administration of a treatment modality with a selected state, e.g., being under general anesthesia, or while a second treatment modality is administered, or is present at a preselected level, e.g., a therapeutic level, means that administration of the treatment modality overlaps or occurs at the same time as, e.g., administration of a second treatment modality.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, "general anesthesia" or "GA" is a state produced when a subject receives medications for e.g., amnesia, analgesia, muscle paralysis, and sedation. For example, GA is a treatment that induces deep sleep typically used so that subjects will not feel pain during surgery. An anesthetized patient can be thought of as being in a reversible and controlled state of unconsciousness. GA agents can be administered intravenously or inhaled.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Therapeutic Agents
Neuroactive Steroids

Neuroactive steroids (or neurosteroids) are natural, synthetic, or semi-synthetic steroids that rapidly alter neuronal excitability through interaction with neurotransmitter-gated ion channels. Neuroactive steroids effect binding to membrane-bound receptors such as those for inhibitory and (or) excitatory neurotransmitters including $GABA_A$, NMDA, and sigma receptors.

The steroids that may be classified into functional groups according to chemical structure and physiological activity and include estrogenic hormones, progestational hormones, and androgenic hormones. Of particular interest are progestational hormones, referred to herein as "progestins" or "progestogens", and their derivatives and bioactive metabolites. Members of this broad family include steroid hormones disclosed in Remington's Pharmaceutical Sciences, Gennaro et al., Mack Publishing Co. (18th ed. 1990), 990-993. As with all other classes of steroids, stereoisomerism is of fundamental importance with the sex hormones. As used herein, a variety of progestins (e.g., progesterone) and their derivatives, including both synthetic and natural products, can be used, as well as progestin metabolites such as progesterone.

The term "progesterone" as used herein refers to a member of the progestin family and includes a 21 carbon steroid hormone. Progesterone is also known as D4-pregnene-3,20-dione; Δ4-pregnene-3,20-dione; or pregn-4-ene-3,20-dione. As used herein a "synthetic progestin" is a molecule whose structure is related to that of progesterone, is synthetically derived, and retains the biological activity of progesterone.

Representative synthetic progestins include, but are not limited to, substitutions at the 17-position of the progesterone ring to introduce a hydroxyl, acetyl, hydroxyl acetyl, aliphatic, nitro, or heterocyclic group, modifications to produce 17α-OH esters (e.g., 17 α-hydroxyprogesterone caproate), as well as modifications that introduce 6-methyl, 6-ene, and 6-chloro substituents onto progesterone (e.g., medroxyprogesterone acetate, megestrol acetate, and chlomadinone acetate), and which retains the biological activity of progesterone. Such progestin derivatives include 5-dehydroprogesterone, 6-dehydro-retroprogesterone (dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy); levonorgestrel, norethindrone, norethindrone acetate (19-norpregn-4-en-20-yn-3-one, 17-(acetyloxy)-,(17α)-); norethynodrel, norgestrel, pregnenolone, and megestrol acetate.

Useful progestins also can include allopregnone-3α or 3β, 20α or 20β-diol (see Merck Index 258-261); allopregnane-3β, 21-diol-11,20-dione; allopregnane-3β, 17α-diol-20-one; 3,20-allopregnanedione, allopregnane, 3β, 11β, 17α, 20β, 21-pentol; allopregnane-3β, 17α, 20β, 21-tetrol; allopregnane-3α or 3β, 11β, 17α, 21-tetrol-20-one, allopregnane-3β, 17α or 20β-triol; allopregnane-3β, 17α, 21-triol-11,20-dione; allopregnane-3β, 11β, 21-triol-20-one; allopregnane-3β, 17α, 21-triol-20-one; allopregnane-3α or 3β-ol-20-one; pregnanediol; 3,20-pregnanedione; pregnan-3α-ol-20-one; 4-pregnene-20,21-diol-3,11-dione; 4-pregnene-11β, 17α, 20β, 21-tetrol-3-one; 4-pregnene-17α, 20β, 21-triol-3,11-dione; 4-pregnene-17α, 20β, 21-triol-3-one, and pregnenolone methyl ether. Further progestin derivatives include esters with non-toxic organic acids such as acetic acid, benzoic acid, maleic acid, malic acid, caproic acid, and citric acid and inorganic salts such as hydrochloride, sulfate, nitrate, bicarbonate and carbonate salts. Other suitable progestins include alphaxalone, alphadolone, hydroxydione, and minaxolone.

Additional suitable neuroactive steroids are disclosed in United States Patent Application Publication Nos. US 2011/0092473 and US 2010/0317638, and U.S. Pat. No. 5,232,917, which are incorporated herein by reference for the neuroactive steroids described therein.

In particular embodiments, the steroids are one or more of a series of sedative-hypnotic 3 alpha-hydroxy ring A-reduced pregnane steroids that include the major metabolites of progesterone and deoxycorticosterone, 3 alpha-hydroxy-5 alpha-pregnan-20-one (allopregnanolone) and 3 alpha,21-dihydroxy-5 alpha-pregnan-20-one (allotetrahydroDOC), respectively. These 3 alpha-hydroxysteroids do not interact with classical intracellular steroid receptors but bind stereoselectively and with high affinity to receptors for the major inhibitory neurotransmitter in the brain, gamma-amino-butyric acid (GABA).

In certain embodiments, the neuroactive steroids are progesterone, allopregnanolone or other progesterone analogs. In a particular embodiment, the neuroactive steroid is allopregnanolone or a derivative thereof. Exemplary derivatives include, but are not limited to, (20R)-17beta-(1-hydroxy-2,3-butadienyl)-5alpha-androstane-3alpha-ol (HBAO). Additional derivatives are described in WO 2012/127176.

As used herein "allopregnanolone" also encompasses pharmaceutically acceptable, pharmacologically active derivatives including individual enantiomers (dextrogyral and levrogyral enantiomers) and their pharmaceutically acceptable salts, mixtures of enantiomers and their pharmaceutically acceptable salts, and active metabolites and their pharmaceutically acceptable salts, unless otherwise noted. It is understood that in some cases dosages of enantiomers, derivatives, and metabolites may need to be adjusted based on relative activity of the racemic mixture of allopregnanolone.

The lipophilic nature of allopregnanolone can make it different to formulate for in vivo administration. As discussed above, allopregnanolone can be formulated with a host, such as a cyclodextrin to improve the solubility. Alternatively, or additionally, allopregnanolone can be modified in an attempt to improve the solubility. For example, polar groups can be introduced onto position 16a with the goal of increasing water solubility, brain accessibility, and potency of neuroactive steroids as described in Kasal et al., *J. Med. Chem.*, 52(7), 2119-215 (2009).

In some embodiments, the compounds described herein (e.g., allopregnanolone), is administered to a subject under general anesthesia.

Anesthetics and Sedatives

An anesthetic (e.g., general anesthetic) agent or sedative is a drug that can bring about, induce, and maintain a reversible loss of consciousness. A sedative is a substance that induces sedation by reducing irritability or excitement in a subject. Intravenous injections of anesthetics are generally preferred to inhalation, intramuscular or subcutaneous injections because they are faster, generally less painful and more reliable. Exemplary anesthetics include propofol, etomidate, barbiturates (e.g., pentobarbital, methohexital, thiopentone/thiopental), benzodiazepines (e.g., as described herein, e.g., midazolam), and ketamine.

In some embodiments, a subject that has been administered an anesthetic agent or anesthetic is under general anesthesia.

Benzodiazepines

A benzodiazepine is a compound having a core chemical structure of a fusion of a benzene ring and a diazepine ring. The first benzodiazepine, chlordiazepoxide, was discovered in 1955. Benzodiazepines can enhance the effect of the neurotransmitter gamma-aminobutyric acid (GABA) at the $GABA_A$ receptor, and can result in sedative, hypnotic (sleep-inducing), anxiolytic (anti-anxiety), anticonvulsant, or muscle relaxant properties. Benzodiazepines are categorized as either short-, intermediate- or long-acting. Exemplary benzodiazapines include alprazolam, bretazenil, bromazepam, brotizolam, chloridazepoxide, cinolazepam, clonazepam, chorazepate, clotiazepam, cloxazolam, delorazepam, diazepam, estazolam, etizolam, ethyl loflazepate, flunitrazepam, flurazepam, flutoprazepam, halazepam, ketazolam, loprazolam, lorazepam, lormetazepam, medazepam, midazolam, nimetazepam, nitrazepam, nordazepam, oxazepam, phenazepam, pinazepam, prazepam, premazepam, pyrazolam, quazepam, temazepam, tatrazepam, and triazolam.

A commonly used anesthetic agent is midazolam. In some embodiments, the benzodiazepine is midazolam.

Barbiturates

Barbiturates are drugs that have been used as CNS depressants and used e.g., to induce mild sedation, total anesthesia; and used as an anxiolytic, hypnotic, anticonvulsant, analgesic. Side effects of barbiturates include addiction potential, e.g., physical and psychological addiction. Barbiturates may be classified as e.g., ultrashort-acting, short/intermediate-acting, and long-acting. Exemplary barbiturates include pentobarbital, allobarbital, amobarbital, aprobarbital, barbital, brallobarbital.

Propofol

Propofol (2,6-diisopropylphenol) is a drug, administered intravenously, that provides loss of awareness and can be used with other general anesthetic agents. The main advantages are favorable operating conditions and rapid recovery, but have disadvantages that include a relatively high incidence of apnea and blood pressure reductions.

As used herein "neuroactive steroid" also encompasses pharmaceutically acceptable, pharmacologically active derivatives of these agents (e.g., neuroactive steroids including both individual enantiomers of neuroactive steroids (dextrogyral and levrogyral enantiomers)) and their pharmaceutically acceptable salts, mixtures of enantiomers and their pharmaceutically acceptable salts, and active metabolites and their pharmaceutically acceptable salts, unless otherwise noted. It is understood that in some cases dosages of enantiomers, derivatives, and metabolites may need to be adjusted based on relative activity of the racemic mixture.

As used herein, "pharmaceutically acceptable salts" refer to derivatives of the disclosed compounds wherein the parent compound is modified by making the acid-addition or base-addition salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, MD, 2000, p. 704.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Compounds described herein such as neuroactive steroids, generally contain one or more chiral centers, and thus exist as one or more stereoisomers. Such stereoisomers can be prepared and/or isolated as a single enantiomer, a mixture of diastereomers, or a racemic mixture.

As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

Dosage and Pharmacokinetics

The compositions described herein include a therapeutically effective amount of a neuroactive steroid, such as allopregnanolone, and a therapeutically effective amount of a benzodiazepine or anesthetic/sedative. In some embodiments, the neuroactive steroid and benzodiazepine or anesthetic/sedative are co-formulated into a single composition or dosage. In some embodiments, the neuroactive steroid and benzodiazepine or anesthetic/sedative are administered separately. In some embodiments, the neuroactive steroid and benzodiazepine or anesthetic/sedative are administered sequentially. In some embodiments, the neuroactive steroid and benzodiazepine or anesthetic/sedative are administered separately and sequentially. In general, at least one of the neuroactive steroid and benzodiazepine or anesthetic/sedative is administered parenterally (e.g., intranasally, buccally, intravenously or intramuscularly, for example, intramuscular (IM) injection or intravenously). In some embodiments, both the neuroactive steroid and benzodiazepine or anesthetic/sedative is administered parenterally (e.g., intranasally, buccally, intravenously or intramuscularly).

In one embodiment, the neuroactive steroid and/or the benzodiazepine or anesthetic/sedative is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 10 µg to about 10 mg per kg of body weight, from about 100 µg to about 5 mg per kg of body weight, from about 250 µg to about 3 mg per kg of body weight, from about 500 µg to about 2 mg per kg of body weight, from about 1 µg to about 50 mg per kg of body weight, from about 1 µg to about 500 µg per kg of body weight; and from about 1 µg to about 50 µg per kg of body weight. Alternatively, the amount of neuroactive steroid and/or the benzodiazepine or anesthetic/sedative administered to achieve a therapeutic effective dose is about 0.1 ng, 1 ng, 10 ng, 100 ng, 1 µg, 10 µg, 100 µg, 1 mg, 1.5 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In one embodiment, the neuroactive steroid is administered as an intravenous bolus infusion in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 10 µg to about 5 mg per kg of body weight, from about 100 µg to about 500 µg per kg of body weight, from about 100 µg to about 400 µg per kg of body weight, from about 150 µg to about 350 µg per kg of body weight, from about 250 µg to about 300 µg per kg of body weight. In one embodiment, the neuroactive steroid is administered as an intravenous bolus infusion in a dose equivalent to parenteral administration of about 100 to about 400 µg/kg. In some embodiments, the neuroactive steroid is administered as an intravenous bolus infusion at about 150 to about 350 µg/kg. In some embodiments, the neuroactive steroid is administered as an intravenous bolus infusion at about 250 to about 300 µg/kg. In specific embodiments, the neuroactive steroid is administered as an intravenous bolus infusion in a dose equivalent to about 100 µg/kg, 125 µg/kg, 150 µg/kg, 175 µg/kg, 200 µg/kg, 225 µg/kg, 250 µg/kg, 260 µg/kg, 270 µg/kg, 280 µg/kg, 290 µg/kg, 300 µg/kg, 325 µg/kg, or 350 µg/kg.

In one embodiment, the neuroactive steroid is administered as an intravenous bolus infusion in a dose equivalent to parenteral administration of about 0.1 nmoles/L to about 100 µmoles/L per kg of body weight, about 1 nmoles/L to about 10 µmoles/L per kg of body weight, about 10 nmoles/L to about 10 µmoles/L per kg of body weight, about 100 nmoles/L to about 10 µmoles/L per kg of body weight, about 300 nmoles/L to about 5 µmoles/L per kg of body weight, about 500 nmoles/L to about 5 µmoles/L per kg of body weight, and about 750 nmoles/L to about 1 µmoles/L per kg of body weight, Alternatively, the amount of neuroactive steroid administered to achieve a therapeutic effective dose is about 0.1 ng, 1 ng, 10 ng, 100 ng, 1 µg, 10 µg, 100 µg, 1 mg, 1.5 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 40 mg, 50 mg, 60 mg, 70 mg, 80 mg, 90 mg, 100 mg, 500 mg per kg of body weight or greater.

In some embodiments, the neuroactive steroid and/or the benzodiazepine or anesthetic/sedative may be administered once or several times a day. A duration of treatment may follow, for example, once per day for a period of about 1, 2, 3, 4, 5, 6, 7 days or more. In some embodiments, either a single dose in the form of an individual dosage unit or several smaller dosage units or by multiple administration of subdivided dosages at certain intervals is administered. For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 1.5, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the subject from the secondary wave of edema that may occur over the first several days post-injury.

Area under the curve (AUC) refers to the area under the curve that tracks the serum concentration (nmol/L) of neuroactive steroid and/or the benzodiazepine or anesthetic/sedative over a given time following the IV administration of the reference neuroactive steroid or the benzodiazepine or anesthetic/sedative standard. By "reference neuroactive steroid" or "benzodiazepine standard" or "anesthetic/sedative standard" is intended the formulation of neuroactive steroid or the benzodiazepine or anesthetic/sedative that serves as the basis for determination of the total hourly neuroactive steroid and/or the benzodiazepine or anesthetic/sedative dose to be administered to a human subject with epilepsy or status epilepticus to achieve the desired positive effect, i.e., a positive therapeutic response that is improved with respect to that observed without administration of neuroactive steroid and/or the benzodiazepine or anesthetic/sedative. In an embodiment, the dose of neuroactive steroid and/or the benzodiazepine or anesthetic/sedative to be administered provides a final serum level of neuroactive steroid and/or the benzodiazepine or anesthetic/sedative of about 100 ng/mL to about 1000 ng/mL, about 1100 ng/mL to about 1450 ng/mL, 100 ng/mL to about 250 ng/mL, about 200 ng/mL to about 350 ng/mL, about 300 ng/mL to about 450 ng/mL, about 350 ng/mL to about 450 ng/mL, about 400 ng/mL to about 550 ng/mL, about 500 ng/mL to about 650 ng/mL, about 600 ng/mL to about 750 ng/mL, about 700 ng/mL to about 850 ng/mL, about 800 ng/mL to about 950 ng/mL, about 900 ng/mL to about 1050 ng/mL, about 1000 ng/mL to about 1150 ng/mL, about 100 ng/mL to about 1250 ng/mL, about 1200 ng/mL to about 1350 ng/mL, about 1300 ng/mL to about 1500 ng/m. In specific embodiments, the serum level of neuroactive steroid and/or the benzodiazepine or anesthetic/sedative is about 100 ng/mL, 250 ng/mL, 300 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 500 ng/mL, 750 ng/mL, 900 ng/mL, 1200 ng/mL, 1400 ng/mL, or 1600 ng/mL.

In an embodiment, the dose of neuroactive steroid to be administered provides a final serum level of neuroactive steroid of about 100 nmoles/L to about 5000 nmoles/L, about 100 nmoles/L to about 2500 nmoles/L, about 100 nmoles/L to about 1000 nmoles/L, 100 nmoles/L to about 500 nmoles/L, about 100 nmoles/L to about 250 nmoles/L, about 100 nmoles/L to about 200 nmoles/L, about 125 nmoles/L to about 175 nmoles/L. or about 140 nmoles/L to about 160 nmoles/L. In specific embodiments, the serum level of neuroactive steroid and/or the benzodiazepine or anesthetic/sedative is about 100 nmoles/L, 125 nmoles/L, 150 nmoles/L, 175 nmoles/L, 200 nmoles/L, 250 nmoles/L, 300 nmoles/L, 350 nmoles/L, 500 nmoles/L, 750 nmoles/L, 1000 nmoles/L, 1500 nmoles/L, 2000 nmoles/L, 2500 nmoles/L, or 5000 nmoles/L.

In some embodiments, the neuroactive steroid and the benzodiazepine or anesthetic/sedative administration includes a time period in which the administration of the benzodiazepine therapy or anesthetic/sedative is weaned off.

As used herein, "weaning" or "weaning dose" refers to an administration protocol which reduces the dose of administration to the patient and thereby produces a gradual reduction and eventual elimination of the benzodiazepine or anesthetic/sedative, either over a fixed period of time or a time determined empirically by a physician's assessment based on regular monitoring of a therapeutic response of a subject. The period of the weaned benzodiazepine or anesthetic/sedative administration can be about 12, 24, 36, 48 hours or longer. Alternatively, the period of the weaned benzodiazepine or anesthetic/sedative administration can range from about 1 to 12 hours, about 12 to about 48 hours, or about 24 to about 36 hours. In some embodiments, the period of the weaned benzodiazepine or anesthetic/sedative administration is about 24 hours.

The weaning employed could be a "linear" weaning. For example, a "10%" linear weaning from 500 mg would go 500, 450, 400, 350, 300, 250, 200, 150, 100, 50. Alternatively, an exponential weaning could be employed which, if the program outlined above is used as an example, the exponential weaning would be, e.g., 500, 450, 405, 365, 329, 296, 266, 239, etc. Accordingly, about a 5%, 10%, 15%, 20%, 25%, 30%, 35%, or 40% linear or exponential weaning could be employed in the methods of the invention. In addition, a linear or exponential weaning of about 1% to 5%, about 6% to 10%, about 11% to 15%, about 16% to 20%, about 21% to 25%, about 26% to 30%, about 31% to 35%, about 36% to 40% could be employed.

In other embodiments, the neuroactive steroid and the benzodiazepine or anesthetic/sedative administration includes a final time period in which the administration of neuroactive steroid is tapered off.

As used herein, "tapered administration", "tapered dose", and "downward taper dose" refers to an administration protocol which reduces the dose of administration to the patient and thereby produces a gradual reduction and eventual elimination of neuroactive steroid, either over a fixed period of time or a time determined empirically by a physician's assessment based on regular monitoring of a therapeutic response of a subject. The period of the tapered neuroactive steroid administration can be about 12, 24, 36, 48 hours or longer. Alternatively, the period of the tapered neuroactive steroid administration can range from about 1 to 12 hours, about 12 to about 48 hours, or about 24 to about 36 hours. In some embodiments, the period of the tapered neuroactive steroid administration is about 24 hours.

The drug taper employed could be a "linear" taper. For example, a "10%" linear taper from 500 mg would go 500, 450, 400, 350, 300, 250, 200, 150, 100, 50. Alternatively, an exponential taper could be employed which, if the program outlined above is used as an example, the exponential taper would be, e.g., 500, 450, 405, 365, 329, 296, 266, 239, etc. Accordingly, about a 5%, 10%, 15%, 20%, 25%, 30%, 35%, or 40% linear or exponential taper could be employed in the methods of the invention. In addition, a linear or exponential taper of about 1% to 5%, about 6% to 10%, about 11% to 15%, about 16% to 20%, about 21% to 25%, about 26% to 30%, about 31% to 35%, about 36% to 40% could be employed. In some embodiments, the drug taper is a about 25% linear taper.

Where a subject undergoing therapy exhibits a partial response, or a relapse following completion of the first cycle of the therapy, subsequent courses of neuroactive steroid therapy may be needed to achieve a partial or complete therapeutic response. Thus, subsequent to a period of time off from a first treatment period, which may have included a constant neuroactive steroid dosing regimen or a two-level neuroactive steroid and/or the benzodiazepine or anesthetic/sedative dosing regimen, a subject may receive one or more additional treatment periods including either constant or two-level neuroactive steroid and/or the benzodiazepine or anesthetic/sedative dosing regimens. Such a period of time off between treatment periods is referred to herein as a time period of discontinuance. It is recognized that the length of the time period of discontinuance is dependent upon the degree of subject response (i.e., complete versus partial) achieved with any prior treatment periods of the neuroactive steroid.

In some embodiments, the neuroactive steroid is administered as an intravenous infusion for about 5 minutes to about 1 week; about 30 minutes to about 24 hours, about 1 hour to about 12 hours, about 2 hours to about 12 hours, about 4 hours to about 12 hours, about 6 hours to about 12 hours, about 6 hours to about 10 hours; about 5 minutes to about 1 hour, about 5 minutes to about 30 minutes; about 12 hours to about 1 week, about 24 hours to about 1 week, about 2 days to about 5 days, or about 3 days to about 5 days. In one embodiment, the neuroactive steroid is administered as an intravenous infusion for about 5, 10, 15, 30, 45, or 60 minutes or longer; about 1, 2, 4, 6, 8, 10, 12, 16, or 24 hours or longer; about 1, 2, 3, 4, 5, 6, 7, 8, 9, or 10 days or longer.

These multiple treatment sessions are referred to herein as maintenance cycles, where each maintenance cycle includes a completed constant or two-level neuroactive steroid or the benzodiazapine dosing regimen. By "completed two-level progesterone, allopregnanolone, or a synthetic progestin dosing regimen" is intended the subject has been administered both the first period and the second period of neuroactive steroid or the benzodiazapine dosing. The necessity for multiple maintenance cycles can be assessed by monitoring the physiological and behavioral improvement of the patient. The duration between maintenance cycles can be about 1 hr, 15 hr, 1 day, 2 day, 3 day, 4 day, 5 day, 6 day or other such time periods falling within the range of about 1 day to about 14 days.

In some embodiments, the maintenance cycle is about 2 days. In some embodiments, the maintenance cycle is about 3 days. In some embodiments, the maintenance cycle is about 4 days. In some embodiments, the maintenance cycle is about 5 days.

In some embodiments, the maintenance cycle begins from about 30 minutes to about 24 hours, about 30 minutes to about 12 hours, about 30 minutes to about 8 hours, about 30 minutes to about 4 hours, about 30 minutes to about 2 hours, about 30 minutes to about 1 hour following the initial bolus infusion administration. In some embodiments, the maintenance cycle begins 30 minutes, 45 minutes, 1 hour, 2 hours, 3 hours, 4 hours, 6 hours, 8 hours, 12 hours, 24 hours, or longer following the initial bolus infusion administration.

In one embodiment, the maintenance cycle the neuroactive steroid is administered as an intravenous infusion at an amount of neuroactive steroid/unit time of about 20 to about 5000 µg/kg/hr. In some embodiments, the maintenance cycle the neuroactive steroid is administered as an intravenous infusion at an amount of neuroactive steroid/unit time of about 20 to about 2500 µg/kg/hr. In some embodiments, the maintenance cycle the neuroactive steroid is administered as an intravenous infusion at an amount of neuroactive steroid/unit time of about 20 to about 500 µg/kg/hr. In some embodiments, the neuroactive steroid is administered as an intravenous infusion at a rate of about 20 to about 250 µg/kg/hr. In some embodiments, the neuroactive steroid is administered as an intravenous infusion at an amount of neuroactive steroid/unit time of about 20 to about 200 µg/kg/hr. In some embodiments, the neuroactive steroid is administered as an intravenous infusion at an amount of neuroactive steroid/unit time of about 20 to about 150 µg/kg/hr. In some embodiments, the neuroactive steroid is administered as an intravenous infusion at an amount of neuroactive steroid/unit time of about 50 to about 100 µg/kg/hr. In some embodiments, the neuroactive steroid is administered as an intravenous infusion at an amount of neuroactive steroid/unit time of about 70 to about 100 µg/kg/hr. In specific embodiments, the neuroactive steroid is administered as an intravenous infusion at an amount of neuroactive steroid/unit time of about 25 µg/kg/hr, 50 µg/kg/hr, 75 µg/kg/hr, 80 µg/kg/hr, 85 µg/kg/hr, 86 µg/kg/hr, 87 µg/kg/hr, 88 µg/kg/hr, 89 µg/kg/hr, 90 µg/kg/hr, 100 µg/kg/hr, 125 µg/kg/hr, 150 µg/kg/hr, or 200 µg/kg/hr.

In one embodiment, the neuroactive steroid is administered as an intravenous infusion in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 10 µg to about 5 mg per kg of body weight; and from about 100 µg to about 1000 µg per kg of body weight. In one embodiment, the neuroactive steroid is administered as an intravenous infusion in a dose equivalent to parenteral administration of about 0.1 nmoles/L to about 100 µmoles/L per kg of body weight, about 1 nmoles/L to about 10 µmoles/L per kg of body weight, about 10 nmoles/L to about 10 µmoles/L per kg of body weight, about 100 nmoles/L to about 10 µmoles/L per kg of body weight, about 300 nmoles/L to about 5 µmoles/L per kg of body weight, about 500 nmoles/L to about 5 µmoles/L per kg of body weight, and about 750 nmoles/L to about 5 µmoles/L per kg of body weight, Alternatively, the amount of neuroactive steroid administered to achieve a therapeutic effective dose is about 0.1 ng, 1 ng, 10 ng, 100 ng, 1 µg, 10 µg, 100 µg, 1 mg, 1.5 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 40 mg, 50 mg, 60 mg, 70 mg, 80 mg, 90 mg, 100 mg, 500 mg per kg of body weight or greater.

As used herein, "about" means approximately plus or minus ten percent.

Formulations

Formulations described herein include a neuroactive steroid and/or a benzodiazepine or anesthetic/sedative in combination with one or more pharmaceutically acceptable excipients. In some embodiments, a formulation includes both a neuroactive steroid and a benzodiazepine or anesthetic/sedative.

Matrix-Forming Materials

Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

Solubilization of Neuroactive Steroids

Many neuroactive steroids possess limited aqueous solubility. In order to provide formulations capable of delivering therapeutically effective dosages, a variety of methods can be employed to enhance the solubility and bioavailability of neuroactive steroids. See, for example, "Water-Insoluble Drug Formulation", 2nd Edition, edited by Rong Liu (CRC Press, Boca Raton, FL, 2008). Using the techniques described below, a solubilized formulation of one or more neuroactive steroids can be prepared. These solubilized formulations can be further incorporated into the parenteral and non-parenteral formulations described in sections 2 and 3.

Inclusion Complexes

The solubility of neuroactive steroids can be improved by inclusion complexation (e.g., host-guest formulations). Inclusion complexes are formed when a nonpolar molecule (i.e., the guest, such as a drug with poor aqueous stability) or portion of a molecule inserts into a nonpolar cavity of another molecule or group of molecules (i.e., the host). If the host molecule or molecules exhibit water good solubility, the solubility of the host-guest complex will be greater than the solubility of the guest alone.

Inclusion complexes containing or comprising one or more neuroactive steroids can be formed using any suitable host molecule or molecules. For example, the water solubility of neuroactive steroids can be increased by inclusion complexation with cyclodextrins. Steroid-cyclodextrin complexes are known in the art. See, for example, U.S. Pat. No. 7,569,557 to Backensfeld, et al., and U.S. Patent Application Publication No. US 2006/0058262 to Zoppetti, et al.

Dextrans are soluble polysaccharides produced by bacteria and yeasts. They are characterized by a predominance (>95%) of α (1-6) backbone linkages and varying proportions of α(1-2), α(1-3) and α(1-4) linkages typically at branch points 1, 2. Dextrins are partially hydrolyzed glucose homopolymers composed exclusively of α(1-4) backbone linkages.

Cyclodextrins are cyclic oligosaccharides containing or comprising six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a hydrophobic drug, such as a neuroactive steroid, the neuroactive steroid (i.e., the guest) inserts into the hydrophobic interior of the cyclodextrin (i.e., the host). The host-guest complex retains water solubility as a consequence of the hydrophobic exterior of the cyclodextrin ring.

Neuroactive steroid-cyclodextrin complexes can, as solubility permits, be incorporated into any of the parenteral and non-parenteral formulations described below. If desired, the aqueous solubility of solid neuoractive steroid-cyclodextrin complexes can be further enhanced by isolating the neuoractive steroid-cyclodextrin complex as a solid via lyophilization and/or via micronizing the solid neuroactive steroid-cyclodextrin complex.

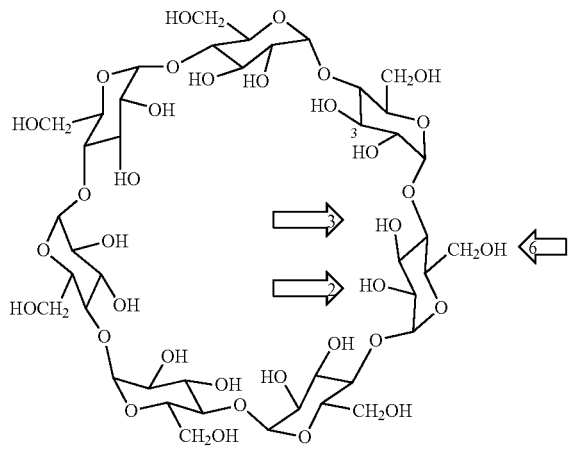

This cyclic orientation provides a truncated cone structure that is hydrophilic on the exterior and lipophilic on the interior. Cyclodextrin complexes are formed when a guest molecule is partially or fully contained in the interior of the cavity. The parent α-, β-, and γ-cyclodextrins (particularly β) have limited aqueous solubility and show toxicity when given parenterally. Therefore, the parent cyclodextrin structure can be chemically modified to generate a parenterally safe CD-derivative. The modifications are typically made at one or more of the 2, 3, or 6 position hydroxyls.

Neuroactive steroid-cyclodextrin complexes are preferably formed from a cyclodextrin selected from the group consisting of α-cyclodextrin, β-cyclodextrin, γ-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo; or a combination thereof. Methods of modifying these alcohol residues are known in the art, and many cyclodextrin derivatives are commercially available, including sulfo butyl ether β-cyclodextrins available under the trade name CAPTISOL® from Ligand Pharmaceuticals (La Jolla, CA).

Examples of suitable cyclodextrins for use in neuroactive steroid, e.g., allopregnanolone formulations, can include cyclodextrins disclosed in U.S. Pat. Nos. 5,874,418; 6,046,177; and 7,635,733, which are herein incorporated by reference. Other examples of suitable cyclodextrins for use in neuroactive steroid formulations non-exclusively include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include, but are not limited to, alkyl cyclodextrins, hydroxy alkyl cyclodextrins, such as hydroxy propyl β-cyclodextrin, carboxy alkyl cyclodextrins and sulfoalkyl ether cyclodextrins, such as sulfo butyl ether β-cyclodextrin.

In particular embodiments, the cyclodextrin is a alpha, beta, or gamma cyclodextrin having a plurality of charges (e.g., negative or positive) on the surface. In more particular embodiments, the cyclodextrin is a β-cyclodextrin containing or comprising a plurality of functional groups that are negatively charged at physiological pH. Examples of such functional groups include, but are not limited to, carboxylic acid (carboxylate) groups, sulfonate ($RSO_3^-$), phosphonate groups, phosphinate groups, and amino acids that are negatively charged at physiological pH. The charged functional groups can be bound directly to the cyclodextrins or can be linked by a spacer, such as an alkylene chain. The number of carbon atoms in the alkylene chain can be varied, but is generally between about 1 and 10 carbons, preferably 1-6 carbons, more preferably 1-4 carbons. Highly sulfated cyclodextrins are described in U.S. Pat. No. 6,316,613.

In one embodiment, the cyclodextrins is a β-cyclodextrin functionalized with a plurality of sulfobutyl ether groups. Such a cyclodextrins is sold under the trade name CAPTISOL®.

CAPTISOL® is a polyanionic beta-cyclodextrin derivative with a sodium sulfonate salt separated from the lipophilic cavity by a butyl ether spacer group, or sulfobutylether (SBE). CAPTISOL® is not a single chemical species, but comprised of a multitude of polymeric structures of varying degrees of substitution and positional/regional isomers dictated and controlled to a uniform pattern by a patented manufacturing process consistently practiced and improved to control impurities.

CAPTISOL® contains six to seven sulfobutyl ether groups per cyclodextrin molecule. Because of the very low pKa of the sulfonic acid groups, CAPTISOL® carries multiple negative charges at physiologically compatible pH values. The four-carbon butyl chain coupled with repulsion of the end group negative charges allows for an "extension" of the cyclodextrin cavity. This often results in stronger binding to drug candidates than can be achieved using other modified cyclodextrins. It also provides a potential for ionic charge interactions between the cyclodextrin and a positively charged drug molecule. In addition, these derivatives impart exceptional solubility and parenteral safety to the molecule. Relative to beta-cyclodextrin, CAPTISOL® provides higher interaction characteristics and superior water solubility in excess of 100 grams/100 ml, a 50-fold improvement.

In other embodiments, the cyclodextrins has plurality of functional groups that are negatively charged at physiological pH. Suitable positively charged groups include, but are not limited to, quaternary ammonium groups. Exemplary cyclodextrins include, but are not limited to, mono-6(A)- butylammonium-6(A)-deoxy-beta-cyclodextrin tosylate (BuAM-beta-CD) and Amine- and guanidine-derivatised β-cyclodextrin (βCD).

Preferably, the cyclodextrin is present in an amount of from about 0.1% to about 40% w/w of the overall formulation, preferably from about 5% to about 40% w/w, more preferably about 10% to about 40% w/w, most preferably about 10% to about 35% w/w. In certain embodiments, the concentration of the cyclodextrins is from about 15% to about 35% w/w, preferably from about 20% to about 35% w/w, more preferably about 30% to about 35% w/w. In one embodiment, the formulation contains about 1 to about 2, preferably about 1.5 mg neuroactive steroid (e.g., allopregnanolone) per ml of cyclodextrin, e.g., CAPTISOL®.

Ion Exchange Resins

Ion exchange resins (IER) are high molecular weight water insoluble polymers containing or comprising fixed positively or negatively charged functional groups in their matrix, which have an affinity for oppositely charged counter ions. IER are solid insoluble high molecular weight poly electrolytes that can exchange with surrounding medium reversibly and stochiometrically.

IER are Styrene (Di Vinyl Benzene) copolymer containing or comprising

Acidic groups: Carboxylic or sulphonic for Cation E.R.
Basic groups: Quaternary Ammonium for Anion E.R Based on the nature of the ionic species being interchanged, the IE process is known as either cation exchange (CE) or anion exchange (AE). The IE process is competitive in nature. In practice, drug in an ionic form (usually solution) is mixed with the appropriate IER form a complex, known as 'resinate'.

The performance of resinates are governed by several factors, such as:

1. The pH and temperature of the drug solution;
2. The molecular weight and charge intensity of the drug and IER;
3. Geometry;
4. Mixing speed;
5. Ionic strength of the drug solution;
6. Degree of cross linking and particle size of the IER;
7. The nature of solvent; and
8. Contact time between the drug species and the IER.

In general, IER consist of spherical beads of approximately 0.5-1.2 mm in diameter. The most common type is an opaque yellow in color, although other colors are also reported. The constitution of each spherical particle of IER is similar to that of a homogeneous gel. The shrinkage or expansion of the spherical volume that takes place is based on the ionic environment in which the IER is present.

A major drawback of controlled or sustained release systems is dose dumping, resulting in increased risk of toxicity. Ion exchange resins offers better drug retaining properties and prevention of dose dumping. The polymeric (physical) and ionic (chemical) properties of ion exchange resin will release the drugs more uniformly than that of simple matrices (because of physical properties only). Drug loaded onto the strong IER resinates provides simplest form of controlled or sustained release delivery system. Resinates can be filled directly in a capsule, suspended in liquids, suspended in matrices or compressed into tablets. Drug will be slowly released by ion exchange phenomenon and absorbed.

Microencapsulation of resinates provides better control over the drug release for oral or depo release. The absorption of the drug from coated resinates is a consequence of the entry of the counter ions into the coated resinates and release of drug ions from drug resin complex by the ion exchange process and diffusion of drug ions through the membrane into the dissolution medium. Designed release rate at the desired level can be obtained by optimization of coating thickness. Microencapsulation of resinates can be achieved by air suspension coating (Wurster process), interfacial polymerization, solvent evaporation or pan coating.

Modification of the coating of resinates for example, by pretreatment with polyethylene glycol 400, can be used to maintain the geometry and improve coating process. The pretreated resinates are then coated with ethyl cellulose or any other water insoluble polymer. The polyethylene glycol helps in controlling the swelling rate of matrix in water, while an outer ethyl cellulose coating modifies the diffusion pattern of ions in and out of system. A major drawback of controlled or sustained release systems is dose dumping, resulting in increased risk of toxicity. Ion exchange resins offers better drug retaining properties and prevention of dose dumping. The polymeric (physical) and ionic (chemical) properties of ion exchange resin release the drugs more uniformly than that of simple matrices.

Drug loaded onto the strong IER resinates provides simplest form of controlled or sustained release delivery system. Resinates can be filled directly in a capsule, suspended in liquids, suspended in matrices or compressed into tablets. Drug will be slowly released by ion exchange phenomenon and absorbed.

There are a few ion exchange resins suitable for intravenous administration of drug. For example, Shimada, et al., in Jpn J. Antibiot. 1985 September; 38(9):2496-502, describes a clinical study on unmodified intravenous dried ion-exchange resin treated human normal immunoglobulin, SM-4300 that showed efficacy with no obvious antipyretic effect, opsonic effect or healing impairment.

Lipid Carriers

To facilitate the administration of neuroactive steroids possessing poor aqueous solubility, a variety of lipid carriers may be used.

Lipid Emulsions

Neuroactive steroids can be combined suspended or dissolved using a lipid emulsion. Lipid emulsions are known in the art. See, for example, U.S. Pat. No. 6,361,792 to Long, et. al.; U.S. Pat. No. 7,550,155 to Zhang, et al., and U.S. Patent Application Publication No. US 2006/0067952. Lipid emulsions formulations typically include one or more neuroactive steroids, an oil component, an emulsifier, and water.

The oil component can be a monoglyceride, a diglyceride, a triglyceride, or combinations thereof. In some cases, the oil component includes an ester formed between one or more fatty acids and an alcohol other than glycerol. The oil component can be, for example, a vegetable oil such as almond oil, borage oil, black currant seed oil, corn oil, safflower oil, soybean oil, sesame oil, cottonseed oil, peanut oil, olive oil, rapeseed oil, coconut oil, palm oil, canola oil, or combinations thereof. Vegetable oils are typically long-chain triglycerides formed from $C_{14}$-$C_{22}$ fatty acids. The oil component can also include medium chain triglycerides formed from C8-C12 fatty acids, such as Miglyol 812, Crodamol® GTCC-PN, or Neobees M-5 oil.

The emulsifier serves to stabilize the lipid emulsion by preventing separation of the emulsion into individual oil and aqueous phases. Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids. In some cases the emulsifier is a phospholipid.

In some cases, the emulsifier is a vitamin E derivative. Suitable vitamin E derivatives include, but are not limited to, α-tocopheryl oxalate, α-tocopheryl malonate, α-tocopheryl succinate, α-tocopheryl glutarate, α-tocopheryl adipate, α-tocopheryl pimelate, α-tocopheryl suberate, α-tocopheryl azelate, and D-α-tocopheryl polyethylene glycol 1000 succinate (vitamin E TPGS).

Exemplary phospholipids include, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. Preferably, the phospholipid is of natural origin. Naturally occurring phospholipids include soy lecithin, egg lecithin, hydrogenated soy lecithin, hydrogenated egg lecithin, sphingosine, gangliosides, and phytosphingosine, and combinations thereof.

Suitable lipid emulsions generally contain between about 1% and 40% w/v oil component and between about 0.1% and 7.5% w/v emulsifier. Suitable commercially available lipid emulsions include lipid emulsions containing or comprising soybean oil, such as Intralipid® 10%, Intralipid® 20%, and Intralipid® 30%, as well as lipid emulsions containing or comprising a mixture of soybean and safflower oils, such as Liposyn® II 10% and Liposyn® II 20%.

Lipid emulsions can optionally contain one or more additional components. For example, lipid formulations can contain one or more non-aqueous miscible co-solvents, such as an alcohol or glycol. In some preferred formulations, glycerol and/or propylene glycol is present as a co-solvent.

Many lipid emulsions are capable of supporting bacterial growth. Accordingly, in some cases, one or more components may be added to the lipid emulsion formulation to prevent or retard bacterial growth, for example disodium edatate, citric acid, metabisulfate, benzyl alcohol, one or more parabens, chlorobutanol, phenol, sorbic acid, or thimerosal.

Additionally, lipid emulsions can contain one or more agents used to modify or stabilize the pH of the solution, including phosphate buffers, acetate buffers, and citrate buffers.

In one embodiment, the formulation is an oil-in-water emulsion containing or comprising a therapeutically effective amount of one or more neuroactive steroids dissolved in a solution containing or comprising between about 1% w/v and about 25% w/v soybean oil, between about 0.5% and about 7.5% w/v egg yolk phospholipid, and between about 0.5% w/v and about 5% w/v of a miscible co-solvent.

In another embodiment, the formulation is an oil-in-water emulsion containing or comprising a therapeutically effective amount of one or more neuroactive steroids dissolved in a solution containing or comprising between about 1% w/v and about 15% w/v soybean oil, between about 1% w/v and about 15% w/v safflower oil, between about 0.5% and about 7.5% w/v egg phosphatides, and between 0.5% w/v and about 5% w/v of a miscible co-solvent.

Lipid emulsions can be administered as described above, or incorporated into the parenteral formulations described below.

Liposomes

One or more neuroactive steroids can be incorporated into liposomes. As is known in the art, liposomes are generally derived from phospholipids or other lipid substances. See, for example, "Remington—The science and practice of pharmacy", 20th Edition, Jennaro et. al., (Phila, Lippencott, Williams, and Wilkens, 2000).

Liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The disclosed compositions in liposome form can contain, in addition to one or more neuroactive steroids, stabilizers, preservatives, excipients, and other suitable excipients.

Examples of suitable lipids are the phospholipids and the phosphatidylcholines (lecithins), both natural and synthetic. Methods of forming liposomes are known in the art. See, e.g., Prescott, Ed., Methods in Cell Biology, Volume XIV, Academic Press, New York p. 33 et seq., 1976. The liposomes can be cationic liposomes (e.g., based on DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract.

One or more neuroactive steroids can formulated using commercially available liposome preparations such as LIPOFECTIN®, LIPOFECTAMIE® (GIBCO-BRL, Inc., Gaithersburg, Md.), SUPERFECT® (Qiagen, Inc. Hilden, Germany) and TRANSFECTAM® (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

One or more neuroactive steroids can also be formulated using noisomes. Noisomes are multilamellar or unilamellar vesicles involving non-ionic surfactants. An aqueous solution of solute is enclosed by a bilayer resulting from the organization of surfactant macromolecules. Similar to liposomes, noisomes are used in targeted delivery of, for example, anticancer drugs, including methotrexate, doxorubicin, and immunoadjuvants. They are generally understood to be different from transferosomes, vesicles prepared from amphiphilic carbohydrate and amino group containing or comprising polymers, e.g., chitosan.

One or more neuroactive steroids can also be delivered using nanoerythrosomes. Nanoerythrosomes are nano-vesicles made of red blood cells via dialysis through filters of defined pore size. These vesicles can be loaded with one or more neuroactive steroids.

Lipid Nanoemulsions

Lipid nanoemulsions can also be used. Lipid nanoemulsions are known in the art. See, for example, U.S. Patent Application Publication No. US 2007/0207173 to Chen, et al, and U.S. Patent Application Publication No. US 2001/0045050 to Elbayoumi, et al. Lipid nanoemulsions can be prepared by microemulsification of any of the lipid emulsions described above using for example, a high pressure homogenizer, or via a phase inversion temperature method (PIT).

In preferred lipid nanoemulsions containing or comprising neuroactive steroids, vitamin E succinate and/or Vitamin E TPGS are included as emulsifiers.

The lipid nanoemulsion can further be lyophilized if desired. See, for example, U.S. Patent Publication No. US 2011/0015266.

Lipid anoemulsions can be administered as described above, or incorporated into the parenteral or non-parenteral formulations described below.

The pre-concentrate includes an oil phase which has at least one fatty acid oil. Fatty acid oils of the present invention include at least one polyunsaturated fatty acid. The term "polyunsaturated fatty acid" include those fatty acids having at least 50 weight percent or more of polyunsaturated fatty acids. Polyunsaturated fat can be found in grain products, fish and sea food (herring, salmon, mackerel, halibut), soybeans, and fish oil. Polyunsaturated fatty acids include omega-3 fatty acids and omega-6 fatty acids. Polyunsaturated fatty acids include linolic acid and linolenic acid. Preferable polyunsaturated fatty acids include eicosapentaenoic acid, salts of eicosapentaenoic acid, docosahexaenoic acid, salts of docosahexaenoic acid, triglycerides of eicosapentaenoic acid, triglycerides of docosahexaenoic acid, ethyl esters of eicosapentaenoic acid, or ethyl esters of docosahexaenoic acid.

Polyunsaturated fatty acids include omega-3 fatty acid oils and medium chain triglycerides (MCT). A medium chain triglyceride contains about 6 to 14 carbon atoms, preferably about 8 to 12 carbon atoms are suitable for use in the oil phase. Preferable medium chain glyceride includes, for example, caprylic/capric triglyceride such as "Migriol 810", "Migriol 812" (both trade names, manufactured by Huls Co., Ltd., available from Mitsuba Trading Co., Ltd.), a glyceryl tricaprylate (tricaprylin) such as "Panasate 800" (trade name, manufactured by NOF Corporation, Japan).

The pre-concentrate includes an emulsifier component. The emulsifier component has one or more surfactants. Surfactants include any molecule having both a polar head group, which energetically prefers solvation by water, and a hydrophobic tail that is not well solvated by water. The ratio of the oil phase to the emulsifier component is important for the toxicity of the nanoemulsion prepared from the pre-concentrate. Surfactants suitable for use with the pre-concentrate and emulsion include a variety of anionic and nonionic surfactants, as well as other emulsifying compounds that are capable of promoting the formation of oil-in-water emulsions; so long as they are on the GRAS (Generally Recognized as Safe) list and are approved for human consumption such as lecithin, solutol HS-15 (polyoxyethylene esters of 12-hydroxystearic acid), polysorbate 80 or Cremophore EL (polyethoxylated castor oil). See McCutcheon's Volume 1: Emulsifiers and Detergents North American Edition, 1996 (incorporated herein by reference).

Formulations for Parenteral Administration

The compounds (e.g., allopregnanolone) described herein can be formulated for parenteral administration. Preferred doses, dosage forms, or modes of administration are parenteral, e.g., intranasally, buccally, intravenous, intramuscular, subcutaneous, intraparenteral, bucosal, sublingual, intraocular, and topical (e.g., intravenous or intramuscular). In another embodiment, the informational material can include instructions to administer the compound described herein to a suitable subject, e.g., a human, e.g., a human having or at risk for a disorder described herein. In some preferred embodiments, at least one of the neuroactive steroid and benzodiazepine or anesthetic/sedative is formulated for parenteral administration. In some embodiments, both the neuroactive steroid and the benzodiazepine or anesthetic/sedative are formulated for parenteral administration.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

In some embodiments, the parenteral formulations are prepared as an injectable formulation, e.g., for intravenous administration. In some embodiments, the parenteral formulation comprises a compound (e.g., a neurosteroid as described herein, e.g., allopregnanolone), and a cyclodextrin, e.g., a β-cyclodextrin, e.g., a sulfo butyl ether β-cyclodextrin, e.g., CAPTISOL®). In some embodiments, the parenteral formulation comprises allopregnanolone and a sulfo butyl ether β-cyclodextrin, e.g., CAPTISOL®.

The carrier can be a solvent or dispersion medium containing or comprising, for example, water (e.g., Water for Injection, USP), ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

In some embodiments, at least one of the neuroactive steroid or the benzodiazepine or anesthetic/sedative is formulated for intranasal, buccal, intramuscular or intravenous administration (e.g., intramuscular or intravenous administration). In some embodiments, both of the neuroactive steroid and the benzodiazepine or anesthetic/sedative are formulated for intranasal, buccal, intramuscular or intravenous administration (e.g., intramuscular or intravenous administration).

The parenteral formulations described herein can be formulated for controlled release including immediate release, delayed release, extended release, pulsatile release, and combinations thereof.

Nano- and Microparticles

For parenteral administration, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing or comprising microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing or comprising microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing or comprising microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing or comprising microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing or comprising microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing or comprising microparticles or drug particles, a water soluble protein can be spray coated onto the microparticles and subsequently cross-linked by the one of the methods described above. Alternatively, drug containing or comprising microparticles can be microencapsulated within protein by coacervation-phase separation (for example, by the addition of salts) and subsequently cross-linked. Some suitable proteins for this purpose include gelatin, albumin, casein, and gluten. Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In some embodiments, at least one of the neuroactive steroid and/or the benzodiazepine or anesthetic/sedative is formulated for intranasal, buccal, intramuscular or intravenous administration (e.g., intramuscular or intravenous administration). In some embodiments, both of the neuroactive steroid and the benzodiazepine or anesthetic/sedative are formulated for intranasal, buccal, intramuscular or intravenous administration (e.g., intramuscular or intravenous administration).

The compounds described herein can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof.

In depot formulations containing or comprising a polymeric or oligomeric carrier, the carrier and active agent can be formulated as a solution, an emulsion, or suspension. One or more neuroactive steroids, and optionally one or more additional active agents, can also be incorporated into polymeric or oligomeric microparticles, nanoparticles, or combinations thereof.

In some cases, the formulation is fluid and designed to solidify or gel (i.e., forming a hydrogel or organogel) upon injection. This can result from a change in solubility of the composition upon injection, or for example, by injecting a pre-polymer mixed with an initiator and/or cross-linking agent. The polymer matrix, polymer solution, or polymeric particles entrap the active agent at the injection site. As the polymeric carrier is gradually degraded, the active agent is released, either by diffusion of the agent out of the matrix and/or dissipation of the matrix as it is absorbed. The release rate of the active agent from the injection site can be controlled by varying, for example, the chemical composition, molecular weight, crosslink density, and concentration of the polymeric carrier. Examples of such systems include those described in U.S. Pat. Nos. 4,938,763, 5,480,656 and 6,113,943.

Depot formulations can also be prepared by using other rate-controlling excipients, including hydrophobic materials, including acceptable oils (e.g., peanut oil, corn oil, sesame oil, cottonseed oil, etc.) and phospholipids, ion-exchange resins, and sparingly soluble carriers.

The depot formulation can further contain a solvent or dispersion medium containing or comprising, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of a neuroactive steroid or a benzodiazepine or anesthetic/sedative as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

In some embodiments, at least one of the neuroactive steroid and/or the benzodiazepine or anesthetic/sedative is formulated for intranasal, buccal, intramuscular or intravenous administration (e.g., intramuscular or intravenous administration). In some embodiments, both of the neuroactive steroid and the benzodiazepine or anesthetic/sedative are formulated for intranasal, buccal, intramuscular or intravenous administration (e.g., intramuscular or intravenous administration).

Combinations with Active Compounds

A composition described herein can be administered adjunctively with other active compounds such as anesthetics or sedatives, e.g., benzodiazepine, e.g., midazalm, propofol, pentobarbital, and ketamine.

Methods of Use

A composition described herein, can be administered to a subject in need thereof, to treat a disorder described herein. Exemplary disorders include epilepsy, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; a seizure, e.g., acute repetitive seizures, cluster seizures.

In some embodiments, a composition described herein (e.g., a composition comprising allopregnanolone), is administered to a subject under general anesthesia.

Seizures and Seizure-Related Disorders

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Publications cited herein and the materials for which they are cited are specifically incorporated by reference.

Status Epilepticus (SE)

Status epilepticus (SE) encompasses a group of disorders all involving persistent or recurring seizures. The standard of care in the United States (US) typically involves initially treating status epilepticus with a benzodiazepine as a first line agent for "early" SE. A recent study showed that 26.6% of patients did not respond to first line midazolam intramuscular (IM) treatment and 36.6% of patients did not respond to lorazepam intravenous (IV) treatment (Silbergleit et al, 2012).

If patients continue to have seizures after administration of the benzodiazepine, they are treated with a second-line anti-epileptic drug for "established" SE, which in the US is generally fos-phenytoin IV or phenytoin IV. If patients continue to have seizures after administration of first and second line drugs, they are said to enter into a stage of "refractory" SE (RSE).

The generally accepted course of therapy for patients in RSE is general anesthesia (GA) with an agent such as midazolam, propofol, pentobarbital, or ketamine. There is no drug approved for RSE and clinical evidence of the comparative efficacy of the commonly used drugs is lacking (Shorvon, 2011). The goal of therapy with these GA agents is to induce an electroencephalographic "burst suppression" state, in an attempt to block the excitotoxic cerebral damage believed to occur as a result of continued seizure activity in the brain. Burst-suppression is an electroencephalography pattern consisting of alternative periods of slow waves of high amplitude (the burst) and periods of a flat electroencephalogram (EEG) (the suppression); it is associated with comatose states of various etiologies and anesthesia (Amzica & Kroeger, 2011). The goal of a therapy is that when a patient is weaned from the general anesthesia, the patient will no longer have clinical or electrographic seizure activity. EEG and EEG terminology is described in Hirsch et al., J. Clin. Neurophysiol. 2013; 30: 1-27, which reference is incorporated in its entirety.

Patients said to be in super-refractory SE (SRSE) or super-refractory generalized SE are a subgroup of RSE patients who have continued or recurrent seizures 24 hours or more after the onset of anesthetic therapy; it often seen as the recurrence of seizure activity as the patient is weaned from the anesthetic therapy. It has been estimated that ~15% of patients admitted to hospitals with SE become super-refractory (Shorvon & Ferlisi, 2011).

SE can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

EXAMPLES

Example 1: Formulation of ALLO in Captisol

Four prototypes of Allopregnanolone in Captisol were made: 5 mg/mL, 7.5 mg/mL, 9 mg/mL, and 10 mg/mL of Allopregnanolone in 25% captisol.

All formulations were high shear mixed for 1 hour then placed on a magnetic stir plate for up to 24 hours of mixing.

5 mg/mL—appeared clear colorless within approximately 30 min of high shear mixing. The solution was clear colorless with no visible particulates.

7.5 mg/mL—appeared clear colorless during the high shear mixing. When the solution was finished with the 1 hour high shear mix, it was compared against a black background and there was a fine haze visible. After stir plate mixing overnight, the haze was still visible.

9 mg/mL—the solution was hazy even after completion of the 1 hour high shear mixing. The haze was still visible after 19 hours of mixing.

10 mg/mL—the solution was hazy even after completion of the 1 hour high shear mixing. The haze was still visible after 16 hours of mixing.

The haze appears as a "gradient" to the concentration of the ALLO.

TABLE 1

Description of the physical appearance of ALLO formulations with Captisol

| Formulation | Physical Appearance |
| --- | --- |
| 5.0 mg/ml ALLO, 25% Captisol | Clear Solution |
| 7.5 mg/ml ALLO, 25% Captisol | Very Slightly Hazy |
| 9.0 mg/ml ALLO, 25% Captisol | Slightly Hazy |
| 10.0 mg/ml ALLO, 25% Captisol | Hazy |

Example 2: Study of ALLO Injection in the Treatment of Super-Refractory Status Epilepticus A physician at the Massachusetts General Hospital, Boston, Mass. treated one patient in SRSE with allopregnanolone in a hydroxyl-propyl beta cyclodextrin formulation. The patient was a 23-year-old, previously-healthy, male, college graduate who was started on allopregnanolone on his $92^{nd}$ day of SRSE. Prior to starting allopregnanolone, the patient had an extensive workup, including brain biopsy, for the cause of the SE; the workup was negative and the cause of his seizure activity was yet to be determined.

During his hospital course, the patient had previously been treated with propofol, midazolam, lacosamide, phenytoin, phenobarbital, ketamine, clonazepam, levetiracetam, valproate, pentobarbital, topiramate, steroids, pyridoxine, coq-10, lidocaine, electroconvulsive therapy (ECT), bromides, hypothermia, a ketogenic diet, and acupuncture. Although burst suppression was achieved with the anesthetic agents, all attempts to wean the patient from them met with a renewal of generalized seizure activity; this included an attempted wean 1 week before allopregnanolone was started.

Figure 2:
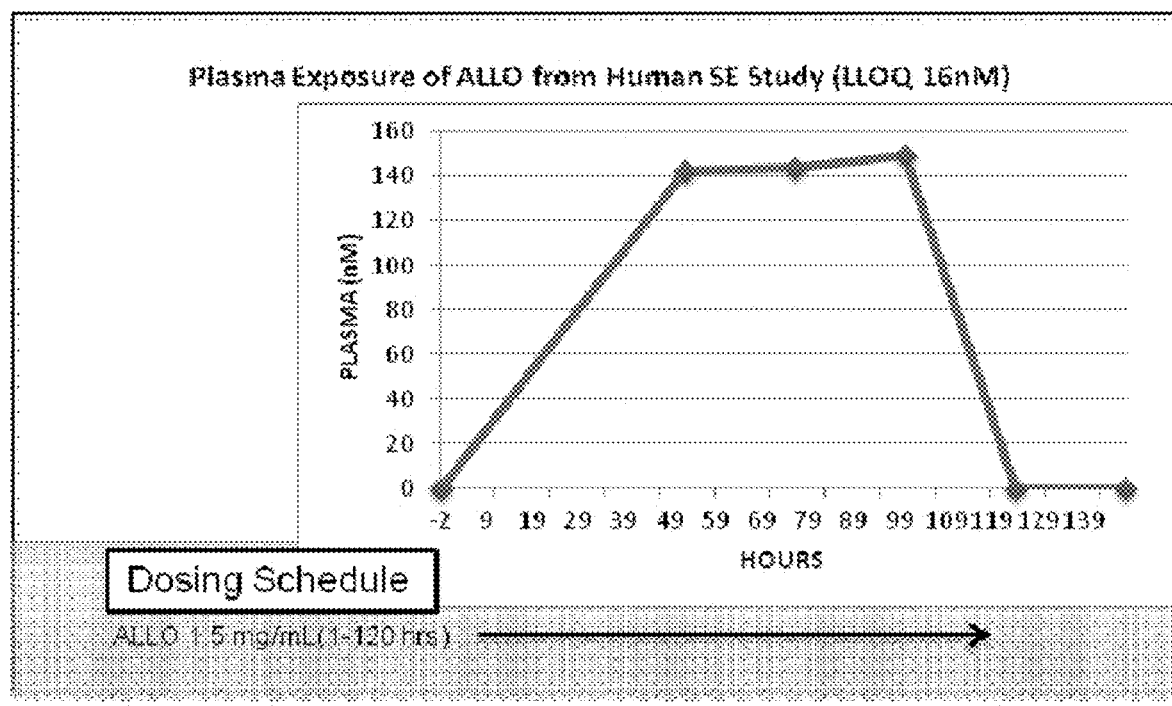
FIG. 2. Plasma exposure of allopregnanolone from human SE study. Plasma concentration profile over time of allopregnanolone in a single male patient. The patient was dosed allopregnanolone (ALLO) at 1.5 mg/mL in 6% hydroxypropyl-β-cyclodextrin in 0.9% sodium chloride intravenously for 5 days (120 h). The infusion rate was 86 μg/kg/h. The patient was dosed 5.6 mg/h of allopregnanolone at 3.8 mL/h. Plasma concentration was analyzed 2 hours prior to the start of infusion and then 52, 76, 100, 124, and 148 hours post-infusion.

At the time that allopregnanolone was started, the patient was still in a pentobarbital-induced coma as well as receiving lacosamide, phenobarbital, clonazepam, and levetiracetam. The patient was started on allopregnanolone at a continuous infusion rate of 86 μg/kg/h for 5 days, after which the allopregnanolone was rapidly tapered and discontinued over a 24-hour period. Plasma samples were drawn at 5 h, 29 h, 53 h, 77 h, 101 h, 125 h, 149 h, and 173 h and are shown on FIG. 2. The plasma level rose and by Day 2 had achieved the target level of 150 nmoles/L. The pentobarbital was tapered and discontinued over the first 36 hours of allopregnanolone therapy. At the 36-hour time point, when patient was entirely weaned from pentobarbital and on allopregnanolone, the EEG had begun to normalize. The EEG continued to improve and at 72 hours the patient was awake and followed simple midline commands. He continued to improve and was conversant, making jokes, and in a rehabilitation facility as of April 2013. There were no adverse events attributed to allopregnanolone.

We claim:

1. A method of preparing a formulation comprising allopregnanolone, said method comprising the step of high shear mixing an aqueous 5 mg/mL solution of allopregnanolone with 25% sulfo butyl ether beta-cyclodextrin solution for a time period of one hour.

2. The method of claim 1, wherein the step of high shear mixing is performed for a time period of one hour, characterized by a clear aqueous solution comprising 5 mg/mL allopregnanolone and 25% sulfo butyl ether beta-cyclodextrin.

3. The method of claim 1, wherein the sulfo butyl ether beta-cyclodextrin includes a sulfo butyl ether beta-cyclodextrin salt.

4. The method of claim 1, wherein the sulfo butyl ether beta-cyclodextrin includes a sulfo butyl ether beta-cyclodextrin sodium salt.

* * * * *